US011386988B2

(12) United States Patent
Johnsson et al.

(10) Patent No.: US 11,386,988 B2
(45) Date of Patent: *Jul. 12, 2022

(54) SYSTEMS AND METHODS FOR DEEP-LEARNING-BASED SEGMENTATION OF COMPOSITE IMAGES

(71) Applicant: EXINI Diagnostics AB, Lund (SE)

(72) Inventors: Kerstin Elsa Maria Johnsson, Lund (SE); Johan Martin Brynolfsson, Helsingborg (SE); Hannicka Maria Eleonora Sahlstedt, Malmö (SE)

(73) Assignee: EXINI Diagnostics AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/020,161

(22) Filed: Sep. 14, 2020

(65) Prior Publication Data
US 2021/0335480 A1 Oct. 28, 2021

Related U.S. Application Data

(63) Continuation-in-part of application No. 17/008,404, filed on Aug. 31, 2020.
(Continued)

(51) Int. Cl.
*G16H 30/40* (2018.01)
*G06T 7/00* (2017.01)
(Continued)

(52) U.S. Cl.
CPC .............. *G16H 30/20* (2018.01); *G06N 3/08* (2013.01); *G06N 20/00* (2019.01); *G06T 7/0012* (2013.01);
(Continued)

(58) Field of Classification Search
CPC .... G06T 7/10; G06T 7/70; G06T 7/50; G06T 2207/30004; G06T 2207/20081;
(Continued)

(56) References Cited

U.S. PATENT DOCUMENTS 7,450,747 B2   11/2008  Jabri et al.
7,751,605 B2   7/2010  Gündel et al.
(Continued)

FOREIGN PATENT DOCUMENTS

CN    101528267 A    9/2009
CN    102361594 A    2/2012
(Continued)

OTHER PUBLICATIONS

American College of Radiology (ACR) and the Society for Pediatric Radiology (SPR), ACR-SPR Practice Parameter for the Performance of Skeletal Scintigraphy (Bone Scan), Resolution 28, (2013-Revused2017), available from: <http://www.acr.org>, 9 pages (2017).
(Continued)

*Primary Examiner* — Amandeep Saini
(74) *Attorney, Agent, or Firm* — Choate, Hall & Stewart LLP; William R. Haulbrook; Ronen Adato

(57) ABSTRACT

Presented herein are systems and methods that provide for improved 3D segmentation of nuclear medicine images using an artificial intelligence-based deep learning approach. For example, in certain embodiments, the machine learning module receives both an anatomical image (e.g., a CT image) and a functional image (e.g., a PET or SPECT image) as input, and generates, as output, a segmentation mask that identifies one or more particular target tissue regions of interest. The two images are interpreted by the machine learning module as separate channels representative of the same volume. Following segmentation, additional analysis can be performed (e.g., hotspot detection/risk assessment within the identified region of interest).

22 Claims, 6 Drawing Sheets
(3 of 6 Drawing Sheet(s) Filed in Color)

Related U.S. Application Data

(60) Provisional application No. 63/014,637, filed on Apr. 23, 2020.

(51) Int. Cl.

| | | |
|---|---|---|
| *G06T 7/187* | (2017.01) | |
| *G06N 20/00* | (2019.01) | |
| *G16H 30/20* | (2018.01) | |
| *G06N 3/08* | (2006.01) | |
| *G06T 15/08* | (2011.01) | |

(52) U.S. Cl.
CPC .............. *G06T 7/187* (2017.01); *G06T 15/08* (2013.01); *G16H 30/40* (2018.01); *G06T 2207/10081* (2013.01); *G06T 2207/10108* (2013.01)

(58) Field of Classification Search
CPC . G06T 2207/10108; G06T 2207/10088; G06T 2207/10104
USPC ........................................................ 382/128
See application file for complete search history.

(56) References Cited

U.S. PATENT DOCUMENTS

| | | | |
|---|---|---|---|
| 7,935,055 | B2 | 5/2011 | Burckhardt |
| 7,970,194 | B2 | 6/2011 | Kimura |
| 8,199,985 | B2 | 6/2012 | Jakobsson et al. |
| 8,211,401 | B2 | 7/2012 | Babich et al. |
| 8,467,856 | B2 | 6/2013 | Renisch et al. |
| 8,538,166 | B2 | 9/2013 | Gordon et al. |
| 8,705,887 | B2 | 4/2014 | Ma et al. |
| 8,778,305 | B2 | 7/2014 | Pomper et al. |
| 8,855,387 | B2 | 10/2014 | Hamadeh et al. |
| 8,962,799 | B2 | 2/2015 | Babich et al. |
| 9,002,081 | B2 | 4/2015 | Brown |
| 9,710,915 | B2 | 7/2017 | Firouzian et al. |
| 9,721,340 | B2 | 8/2017 | Gillies et al. |
| 10,223,610 | B1 | 3/2019 | Akselrod-Ballin et al. |
| 10,311,971 | B2 | 6/2019 | Opfer et al. |
| 10,339,653 | B2 | 7/2019 | Gillies et al. |
| 10,340,044 | B2 | 7/2019 | Yao et al. |
| 10,340,046 | B2 | 7/2019 | Baker |
| RE47,609 | E | 9/2019 | Hamadeh et al. |
| 10,600,184 | B2 | 3/2020 | Golden et al. |
| 10,665,346 | B2 | 5/2020 | Baker |
| 10,748,652 | B2 | 8/2020 | Yao et al. |
| 10,762,993 | B2 | 9/2020 | Baker |
| 10,818,386 | B2 | 10/2020 | Yao et al. |
| 10,943,681 | B2 | 3/2021 | Yao et al. |
| 10,973,486 | B2 | 4/2021 | Sjostrand et al. |
| 11,011,257 | B2 | 5/2021 | Lints et al. |
| 2003/0215120 | A1 | 11/2003 | Uppaluri et al. |
| 2005/0281381 | A1 | 12/2005 | Guendel |
| 2006/0062425 | A1 | 3/2006 | Shen et al. |
| 2006/0064396 | A1 | 3/2006 | Wei et al. |
| 2006/0078183 | A1* | 4/2006 | deCharms ............... A61B 5/055 |
| | | | 382/128 |
| 2007/0081712 | A1 | 4/2007 | Huang et al. |
| 2007/0081713 | A1 | 4/2007 | Jerebko |
| 2007/0100225 | A1 | 5/2007 | Maschke |
| 2007/0115204 | A1 | 5/2007 | Budz et al. |
| 2008/0027315 | A1 | 1/2008 | McGinnis |
| 2009/0309874 | A1 | 12/2009 | Salganicoff et al. |
| 2010/0215581 | A1 | 8/2010 | Hoffmann |
| 2010/0322488 | A1* | 12/2010 | Virtue ....................... G06T 7/11 |
| | | | 382/128 |
| 2011/0063288 | A1 | 3/2011 | Valadez |
| 2011/0255763 | A1 | 10/2011 | Bogoni et al. |
| 2012/0123253 | A1 | 5/2012 | Renisch et al. |
| 2013/0038707 | A1 | 2/2013 | Cunningham et al. |
| 2013/0129168 | A1 | 5/2013 | Ross |
| 2013/0211231 | A1 | 8/2013 | Sundarapandian et al. |
| 2013/0281841 | A1 | 10/2013 | Everett et al. |
| 2015/0110716 | A1 | 4/2015 | Armor |
| 2015/0331995 | A1 | 11/2015 | Zhao et al. |
| 2016/0203263 | A1 | 7/2016 | Maier et al. |
| 2016/0335395 | A1 | 11/2016 | Wu et al. |
| 2017/0083682 | A1 | 3/2017 | McNutt et al. |
| 2018/0144828 | A1 | 5/2018 | Baker |
| 2018/0259608 | A1 | 9/2018 | Golden et al. |
| 2018/0360402 | A1 | 12/2018 | Carmi |
| 2019/0038239 | A1 | 2/2019 | Flohr et al. |
| 2019/0105009 | A1 | 4/2019 | Siemionow et al. |
| 2019/0209116 | A1* | 7/2019 | Sjöstrand ............... A61B 6/466 |
| 2019/0388049 | A1 | 12/2019 | Gupta et al. |
| 2020/0027559 | A1 | 1/2020 | Baker |
| 2020/0051238 | A1 | 2/2020 | El Harouni et al. |
| 2020/0074634 | A1 | 3/2020 | Kecskemethy et al. |
| 2020/0085382 | A1 | 3/2020 | Taerum et al. |
| 2020/0126666 | A1 | 4/2020 | Baker |
| 2020/0193594 | A1 | 6/2020 | Georgescu et al. |
| 2020/0193603 | A1 | 6/2020 | Golden et al. |
| 2020/0245960 | A1 | 8/2020 | Richter et al. |
| 2020/0337658 | A1 | 10/2020 | Sjostrand et al. |
| 2020/0342600 | A1 | 10/2020 | Sjostrand et al. |
| 2020/0352518 | A1 | 11/2020 | Lyman et al. |
| 2020/0357117 | A1 | 11/2020 | Lyman et al. |
| 2020/0357118 | A1 | 11/2020 | Yao et al. |
| 2020/0357521 | A1 | 11/2020 | Baker |
| 2021/0082547 | A1 | 3/2021 | Yao et al. |
| 2021/0093249 | A1 | 4/2021 | Anand et al. |
| 2021/0183485 | A1 | 6/2021 | Yao et al. |
| 2021/0233633 | A1 | 7/2021 | Lints et al. |
| 2021/0334974 | A1 | 10/2021 | Johnsson et al. |

FOREIGN PATENT DOCUMENTS

| | | |
|---|---|---|
| EP | 1426903 A2 | 6/2004 |
| EP | 1508872 A1 | 2/2005 |
| EP | 3043318 A1 | 7/2016 |
| JP | 2010-029481 A | 2/2010 |
| JP | 6013042 B2 | 10/2016 |
| JP | 6170284 B2 | 7/2017 |
| SE | 524500 C2 | 8/2004 |
| WO | WO-99/05503 A2 | 2/1999 |
| WO | WO-2007/062135 A2 | 5/2007 |
| WO | WO-2009/084995 A1 | 7/2009 |
| WO | WO-2011/077303 A1 | 6/2011 |
| WO | WO-2015/058151 A1 | 4/2015 |
| WO | WO-2018/081354 A1 | 5/2018 |
| WO | WO-2019/103912 A2 | 5/2019 |
| WO | WO-2019/136349 A2 | 7/2019 |
| WO | WO-2020/144134 A1 | 7/2020 |
| WO | WO-2020/146032 A1 | 7/2020 |
| WO | WO-2020/190821 A1 | 9/2020 |
| WO | WO-2020/219619 A1 | 10/2020 |
| WO | WO-2020/219620 A1 | 10/2020 |
| WO | WO-2021/061315 A1 | 4/2021 |

OTHER PUBLICATIONS

Anand, A. et al., A Pre-Analytical Validation Study of Automated Bone Scan Index: Effect on Accuracy and Reproducibility Due to the Procedural Variabilities in Bone Scan Image Acquisition. J Nucl Med. pp. 1865-1871, (2016).

Anand, A. et al., Analytic Validation of the Automated Bone Scan Index as an Imaging Biomarker to Standardize Quantitative Changes in Bone Scans of Patients with Metastatic Prostate Cancer, J. Nucl. Med., 57(1):41-45 (2016).

Anand, A. et al., Automated Bone Scan Index as a quantitative imaging biomarker in metastatic castration-resistant prostate cancer patients being treated with enzalutamide, EJNMMI Research, 6:23, 7 pages (2016).

Anand, A. et al., Translating Prostate Cancer Working Group 2 (PCWG2) Progression Criteria into a Quantitative Response Biomarker in Metastatic Castration Resistant Prostate Cancer (mCRPC), ASCO GU Conference, Poster, 1 page, presented Feb. 16, 2017.

Anand, A. et al., Translating Prostate Cancer Working Group 2 (PCWG2) progression criteria into a quantitative response biomarker

(56) References Cited

OTHER PUBLICATIONS in metastatic castration-resistant prostate cancer (mCRPC), Journal of Clinical Oncology, 35(6):170 (2017).
Armstrong, A. et al., Assessment of the bone scan index in a randomized placebo-controlled trial of tasquinimod in men with metastatic castration-resistant prostate cancer (mCRPC), Urologic Oncology: Seminars and Original Investigations, 32:1308-1316 (2014).
Armstrong, A. et al., Development and validation of a prognostic model for overall survival in chemotherapy-naive men with metastatic castration-resistant prostate cancer (mCRPC) from the phase 3 prevail clinical trial, Journal of Clinical Oncology, 35(Suppl. 6):Abstract 138, 5 pages, (2017).
Armstrong, A. J. et al., Phase 3 Assessment of the Automated Bone Scan Index as a Prognostic Imaging Biomarker of Overall Survival in Men with Metastatic Castration-Resistant Prostate Cancer, A Secondary Analysis of a Randomized Clinical Trial. JAMA Oncology 4:944-951, (2018).
Armstrong, A. J. et al., Phase 3 prognostic analysis of the automated bone scan index (aBSI) in men with bone-metastatic castration-resistant prostate cancer (CRPC), Meeting Library ASC University, 11 pages (2017).
Bai, P. et. al., Body region localization in whole-body low-dose CT images of PET/CT scans using virtual landmarks, Medical Physics Wiley USA, 46(3): 1286-1299 (2019).
Belal, S. et al., Association of PET Index quantifying skeletal uptake in NaF PET/CT images with overall survival in prostate cancer patients, ASCO GU 2017, Poster 178, 1 page, presented Feb. 16, 2017.
Belal, S. et al., PET Index quantifying skeletal uptake in NaF PET/CT images with overall survival in prostate cancer patients, ASCO GU 2017, Abstract, 1 page, (Feb. 13, 2017).
Belal, S. L. et al, 3D skeletal uptake of $^{18}$F sodium fluoride in PET/CT images is associate with overall survival in patients with prostate cancer, EJNMMI Research, 7(15):1-8 (2017).
Belal, S.L. et al., Automated evaluation of normal uptake in different skeletal parts in 18F-sodium fluoride (NaF) PET/CT using a new convolutional neural network method, EJNMMI, EANM '17, 44(Suppl 2):S119-S956, Abstract EP-0116 (2017).
Bombardieri, E. et al., Bone scintigraphy: procedure guidelines for tumour imaging, Eur J. Nucl. Med. Mol. Imaging, 30:BP99-BP106, (2003).
Brynolfsson, J., et. al., Deep Learning based urinary bladder segmentation using 18FDCFPyL (PyL-PSMA) PET/CT images, EPS-145, European Association of Nuclear Medicine, (2020), <http://link.springer.com/article/10.1007/s00259-020-04988-4>. pp. S1 and S403-S404, Retrieved Sep. 18, 2020.
Brynolfsson, J., et. al., Deep Learning-Enabled comprehensive detection and quantification of 18FDCFPyL (PyL-PSMA) PET/CT, OP-548, European Association of Nuclear Medicine, (2020), <http://link.springer.com/article/10.1007/s00259-020-04988-4>. pp. S1 and S273, Retrieved Sep. 18, 2020.
Bushberg, J. T. et al., Essential Physics of Medical Imaging, Essential Physics of Medical Imaging, 19.3: p. 581 (table 15-3), p. 713 paragraph 6, section 19.3 and p. 720, (2011).
Capobianco, N. et. al., Whole-body uptake classification and prostate cancer staging in $^{68}$Ga-PSMA-11 PET/CT using dual-tracer learning, European Journal of Nuclear Medicine and Molecular Imaging, (2021), <https://doi.org/10.1007/s00259-021-05473-2> 10 pages. Retrieved on Apr. 18, 2021.
Cha, K. H., et al. Urinary bladder segmentation in CT urography using deep-learning convolutional neural network and level sets, Medical physics, 43(4):1882-1896, (2016).
Ciernik, I. F., et al. 3D-Segmentation of the 18F-choline PET Signal for Target Volume Definition in Radiation Therapy of the Prostate, Technology in cancer research & treatment 6(1): 23-30, (2007).
Dennis, E. et al., Bone Scan Index: A Quantitative Treatment Response Biomarker for Castration-Resistant Metastatic Prostate Cancer, Journal of Clinical Oncology, 30(5):519-524 (2012).

Dertat, A., Applied Deep Learning—Part 4: Convolutional Neural Networks, Towards Data Science,<http://towardsdatascience.com/applied-deep-learning-part-4-convolutional-neural-networks-584bc134de2> 26 pages, (2017).
Eiber, M. et al., Prostate Cancer Molecular Imaging Standardized Evaluation (PROMISE): Proposed miTNM Classification for the Interpretation of PSMA-Ligand PET/CT, The Journal of Nuclear Medicine, 59(3):469-478, (2018).
Fendler, W.P. et. al., $^{68}$Ga-PSMA PET/CT: Joint EANM and SNMMI procedure guideline for prostate cancer imaging: version 1.0, Eur J Nucl Med Mol Imaging, DOI 10.1007/s00259-017-3670-z, 11 pages, (2017).
GE Healthcare, SPECT/CT Cameras, 2 pages, retrieved Oct. 25, 2017: <http://www3.gehealthcare.com.sg/en-gb/products/categories/nuclear_medicine/spect-ct_cameras>.
Giesel, F. L. et al., F-18 labelled PSMA-1007: biodistribution, radiation dosimetry and histopathological validation of tumor lesions in prostate cancer patients, Eur. J. Nucl. Med. Mol. Imaging, 44:678-688 (2017).
Gjertsson, K., et. al., A Novel Automated Deep Learning Algorithm for Segmentation of the Skeleton in Low-Dose CT for [(18)F] DCFPyL PET/CT Hybrid Imaging in Patients with Metastatic Prostate Cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0823, p. S765.
Gjertsson, K., Segmentation in Skeletal Scintigraphy Images using Convolutional Neural Networks, Master's Theses in Mathematical Sciences, pp. 39-58, (2017), <https://lup.lub.lu.se/student-papers/search/publication/8916406>.
Goffin, K. E. et al., Phase 2 study of $^{99m}$Tc-trofolastat SPECT/CT to identify and localize prostate cancer in intermediate- and high-risk patients undergoing radical prostatectomy and extended pelvic lymph node dissection, J. Nucl. Med., 27 pages (2017).
Guimond, A. et al., Average Brain Models: A Convergence Study, Computer Vision and Image Understanding, 77:192-210 (2000).
Hajnal, J. et al., 4.4 Intensity, Size, and Skew Correction; 7.1 Introduction; 7.2 Methods; 7.3 Image Interpretation—General, In: Medical Image Registration, CRC Press LLC, 80-81:144-148 (2001).
Hiller, S. M. et al., $^{99m}$Tc-Labeled Small-Molecule Inhibitors of Prostate-Specific Membrane Antigen for Molecular Imaging of Prostate Cancer, Journal of Nuclear Medicine, 54(8):1369-1376 (2013) retrieved Oct. 25, 2017: <http://jnm.snmjournals.org/content/54/8/1369.full>.
Horikoshi, H. et al., Computer-aided diagnosis system for bone scintigrams from Japanese patients: importance of training database, Annals of Nuclear Medicine, 26(8):622-626 (2012).
Huang, J.-H. et al., A Set of Image Processing Algorithms for Computer-Aided Diagnosis in Nuclear Medicine Whole Body Bone Scan Images, IEEE Transactions on Nuclear Science, 54(3):514-522 (2007).
Im, HJ, et. al., et. al., Current Methods to Define Metabolic Tumor Volume in Positron Emission Tomography: Which One is Better?, Nucl. Med. Mol. Imaging, 52(1):5-15, (2018).
Johnsson, K., et. al., miPSMA Index: Comprehensive and Automated Quantification of $^{18}$F-DCFPyL (PyL-PSMA) PET/CT for Prostate Cancer Staging, J Nucl Med., 61: (Supplement 1) (1435):5 pages, (2020).
Kaboteh R. et al., Progression of bone metastases in patients with prostate cancer—automated detection of new lesions and calculation of bone scan index, EJNMMI Research, 3:64, 6 pages, (2013).
Kaboteh, R. et al., Convolutional neural network based quantification of choline uptake in PET/CT studies is associated with overall survival in patents with prostate cancer, EJNMMI, EANM '17, 44(Suppl 2):S119-S956, Abstract EP-0642 (2017).
Kiess, et al., Prostate-specific membrane antigen and a target for cancer imaging and therapy, The Quarterly Journal of Nuclear Medicine and Molecular Imaging, 59(3):241-268 (2015).
Kikuchi, A. et al., Automated segmentation of the skeleton in whole-body bone scans: influence of difference in atlas, Nuclear Medicine Communications, 33(9):947-953 (2012).
Kinahan, P.E. et al., PET/CT Standardized Update Values (SUVs) in Clinical Practice and Assessing Response to Therapy, Semin Ultra-

(56) References Cited

OTHER PUBLICATIONS sound CT MR 31(6):496-505 (2010) retrieved Oct. 25, 2017: <https://www.ncbi.nlm.nih.gov/pmc/articles/PMC3026294/>.
Knutsson, H., and Andersson, M., Morphons: Segmentation using Elastic Canvas and Paint on Priors, IEEE International Conference on Image Processing (ICIP 2005), Genova, Italy, 4 pages (2005).
Kopka, K. et al., Glu-Ureido-Based Inhibitors of Prostate-Specific Membrane Antigen: Lessons Learned During the Development of a Novel Class of Low-Molecular-Weight Theranostic Radiotracers, The Journal of Nuclear Medicine, 58(9)(Suppl. 2):17S-26S, (2017).
Lin, T.Y. et. al., Feature Pyramid Networks for Object Detection, FAIR, 10 pages, (2016), <https://arxiv.org/abs/1612.03144v1>.
Litjens, G. et al., A survey on deep learning in medical image analysis, Medical Image Analysis, 42:60-88, (2017).
Liu, L. et al., Computer-Aided Detection of Prostate Cancer with MRI: Technology and Applications, Acad Radiol. Author manuscript, 50 pages 2016.
Ma, L. et al., Automatic segmentation of the prostate on CT images using deep learning and multi-atlas fusion, Proc. of SPIE vol. 10133:101332O-1-101332O-9 (2017).
Ma, L. et al., Combining Population and Patient-Specific Characteristics for Prostate Segmentation on 3D CT Images, Proc of SPIE 9784:978427-1-8 (2016).
Ma, L. et al., Random Walk Based Segmentation for the Prostate on 3D Transrectal Ultrasound Images, Proc SPIE Int Soc Opt Eng. Author manuscript, 13 pages (2016).
Mayo Clinic Staff, Choline C-11 PET scan, Overview, Mayo Clinic, 4 pages (2017), retrieved Oct. 25, 2017: <https://www.mayoclinic.org/tests-procedures/choline-c-11-pet-scan/home/ovc-20156994>.
Meyer, A., et. al., Deep learning algorithm improves identification of men with low-risk prostate cancer using PSMA targeted 99mTc-MIP-1404 SPECT/CT, Journal of Clinical Oncology, 37:(15), (2019).
Nakajima, K. et al., Enhanced diagnostic accuracy for quantitative bone scan using an artificial neural network system: a Japanese multi-center database project, EJNMMI Research, 3:83, 9 pages, (2013).
National Cancer Institute, NCI Drug Dictionary: gallium Ga 68-labeled PSMA-11, 1 page, retrieved Oct. 25, 2017: <https://www.cancer.gov/publications/dictionaries/cancer-drug?cdrid=766400>.
National Cancer Institute, NCI Drug Dictionary: technetium Tc 99m methylene diphosphonate, 1 page, retrieved Oct. 25, 2017: <https://www.cancer.gov/publications/dictionaries/cancer-drug?cdrid=537722>.
Nickols, N.G., et. al., A deep learning algorithm to predict coexisting metastatic disease using intraprostatic [F18]DCFPYL PSMA image alone in veterans with prostate cancer, Journal of Clinical Oncology 38, (Supplement 6), 4 pages, 2020.
Ohlsson, M., et. al., Automated Decision Support for Bone Scintigraphy, Computer-based medical systems, pp. 1-6, (2009).
Perera, M. et al., Sensitivity, Specificity, and Predictors of Positive $^{68}$Ga-Prostate-specific Membrane Antigen Positron Emission Tomography in Advanced Prostate Cancer: A Systematic Review and Meta-analysis, European Urology, 70(6):926-937 (2016).
Polymeri, E. et al., Analytical validation of an automated method for segmentation of the prostate gland in CT images, EJNMMI, EANM '17, 44(Suppl 2):S119-S956, Abstract EP-0641 (2017).
Polymeri, E., et. al., Deep learning-based quantification of PET/CT prostate gland uptake: association with overall survival, Clinical Physiology Functional Imaging, DOI: 10.1111/cpf.12611, 40(2):106-113, (2019).
Pouliot, F., et. al., Prospective evaluation of a Novel Deep Learning Algorithm (PSMA-AI) in the assessment of 99mTc-MIP-1404 SPECT/CT in patients with low or intermediate risk prostate cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0804, p. S765.
radiologyinfo.org for Patients, Computed Tomography (CT), 2 pages, retrieved Oct. 25, 2017: <https://www.radiologyinfo.org/en/submenu.cfm?pg=ctscan>.
Ren, S., et. al., Faster R-CNN: Towards Real-Time Object Detection with Region Proposal Networks, 14 pages, (2015), <http://image-net.org/challenges/LSVRC/2015/results>.
Ronneberger, O., et. al., U-Net: Convolutional Networks for Biomedical Image Segmentation, Springer International Publishing, pp. 234-241, (2015), <http://lmb.informatik.uni-freiburg.de/>. Published online on Nov. 18, 2015.
Rowe, S. P. et al., PET Imaging of prostate-specific membrane antigen in prostate cancer: current state of the art and future challenges, Prostate Cancer and Prostatic Diseases, pp. 1-8 (2016).
Rowe, S. P. et al., PSMA-Based [$^{18}$F]DCFPyL PET/CT Is Superior to Conventional Imaging for Lesion Detection in Patients with Metastatic Prostate Cancer, Mol Imaging Biol, 18:411-419, (2016).
Sabbatini, P. et al., Prognostic Significance of Extent of Disease in Bone in Patients With Androgen-Independent Prostate Cancer, Journal of Clinical Oncology, 17(3):948-957 (1999).
Sadik, M. et al., 3D prostate gland uptake of 18F-choline—association with overall survival in patients with hormone-naïve prostate cancer, The Journal of Nuclear Medicine, 58(Suppl. 1):Abstract 544, 2 pages, (2017).
Sadik, M. et al., A new computer-based decision-support system for the interpretation of bone scans, Nuclear Medicine Communications, 27(5):417-423 (2006).
Sadik, M. et al., Automated 3D segmentation of the prostate gland in CT images—a first step towards objective measurements of prostate uptake in PET and SPECT images, Journal of Nuclear Medicine, 58(1):1074, 3 pages, (2017).
Sadik, M. et al., Automated quantification of reference levels in liver and mediastinum (blood pool) for the Deauville therapy response classification using FDG-PET/CT in lymphoma patients, EJNMMI, EANM '17, 44(Suppl 2):S119-S956, Abstract EP-0770 (2017).
Sadik, M. et al., Computer-assisted interpretation of planar whole-body bone scans, Journal Nuclear Medicine, 49(12):1958-65, 2008.
Sadik, M. et al., Convolutional neural networks for segmentation of 49 selected bones in CT images show high reproducibility, EJNMMI, EANM '17, 44(Suppl 2):S119-S956, Abstract OP-657, 2 pages, (2017).
Sadik, M. et al., Improved classifications of planar whole-body bone scans using a computer-assisted diagnosis system: a multicenter, multiple-reader, multiple-case study, Journal of Nuclear Medicine, 50(3): 368-75, 2009.
Sadik, M. et al., Variability in reference levels for Deauville classifications applied to lymphoma patients examined with 18F-FDG-PET/CT, EJNMMI, EANM '17, 44(Suppl 2):S119-S956, Abstract EP-0771 (2017).
Sajn, L. et al., Computerized segmentation of whole-body bone scintigrams and its use in automated diagnostics, Computer Methods and Programs in Biomedicine, 80:47-55 (2005).
Salerno, J. et al., Multiparametric magnetic resonance imaging for pre-treatment local staging of prostate cancer: A Cancer Care Ontario clinical practice guideline, Canadian Urological Association Journal, 10(9-10):332-339 (2016).
Santos-Cuevas, C. et al. $^{99m}$Tc-labeled PSMA inhibitor: Biokinetics and radiation dosimetry in healthy subjects and imaging of prostate cancer tumors in patients, Nuclear Medicine and Biology 52:1-6, (2017).
Sjöstrand K. et al., Statistical regularization of deformation fields for atlas-based segmentation of bone scintigraphy images, MICCAI 5761:664-671 (2009).
Sjöstrand, K., et al., Automated detection and quantification of Prostatic PSMA uptake in SPECT/CT using a Deep Learning Algorithm for Segmentation of Pelvic Anatomy, The Journal of Nuclear Medicine, 59(1):p. 30, (2018).
Sjöstrand, K., et. al., Automated Assessment of Prostatic PSMA Expression in SPECT/CT using Deep Convolutional Neural Networks—A Prospectively Planned Retrospective Analysis of Phase 3 Study MIP-1404-3301, The Journal of Nuclear Medicine, 60 (Supplement 1): Abstract 401, 1 page, (2019).
Sluimer, I. et al., Toward Automated Segmentation of the Pathological Lung in CT, IEEE Transactions on Medical Imaging, 24(8):1025-1038 (2005).

(56) References Cited

OTHER PUBLICATIONS

Tian, Z. et al., A fully automatic multi-atlas based segmentation method for prostate MR images, Proc SPIE Int Soc Opt Eng. Author manuscript, 12 pages (2015).
Tian, Z. et al., A supervoxel-based segmentation method for prostate MR images, Med. Phys., 44(2):558-569 (2017).
Tian, Z. et al., Deep convolutional neural network for prostate MR segmentation, Proc. of SPIE 10135:101351L-1-101351L-6 12 pages, (2017).
Tian, Z., et al., Superpixel-based Segmentation for 3D Prostate MR Images, IEEE Trans Med Imaging, Author manuscript, pp. 558-569, (2016).
Trägårdh, E., et. al., RECOMIA—a cloud-based platform for artificial intelligence research in nuclear medicine and radiology, EJNMMI Physics, <https://doi.org/10.1186/s40658-020-00316-9>, 7:51, 12 pages, (2020).
Ulmert, D. et al., A Novel Automated Platform for Quantifying the Extent of Skeletal Tumour Involvement in Prostate Cancer Patients Using the Bone Scan Index, European Urology, 62(1):78-84 (2012).
Wallis, J.W. et. al., Three-Dimensional Display in Nuclear Medicine, IEEE Trans Med Imaging, 8(4):297-303, (1989).
Wrangsjo, A. et al., Non-rigid Registration Using Morphons, Proceedings of the 14th Scandinavian Conference on Image Analysis (SCIA '05), pp. 501-510 (2005).
Yin, T.-K. and N.T, Chiu, A Computer-Aided Diagnosis for Locating Abnormalities in Bone Scintigraphy by a Fuzzy System With a Three-Step Minimization Approach, IEEE Transactions on Medical Imaging, 23(5):639-654 (2004).

Ali, A. et al., The Automated Bone Scan Index as a Predictor of Response to Prostate Radiotherapy in Men with Newly Diagnosed Metastatic Prostate Cancer: An Exploratory Analysis of STAMPEDE's "M1|RT Comparison", European Urology Oncology 3:412-419. (2020).
Ceci, F. et al., E-PSMA: the EANM standardized reporting guidelines v1.0 for PSMA-PET, European Journal of Nuclear Medicine and Molecular Imaging, 48:1626-1638, (2021).
Johnsson, K. et al., Analytical performance of aPROMISE: automated anatomic contextualization, detection, and quantification of [18F]DCFPyL (PSMA) imaging for standardized reporting, European Journal of Nuclear Medicin and Molecular Imaging, 11 pages, Aug. 31, 2021, doi: 10.1007/s00259-021-05497-8. Epub ahead of print. PMID: 34463809.
Matsubara, N. et al, A Phase II, Randomized, Open-Label, Multi-arm Study of TAS-115 for Castration-Resistant Prostate Cancer Patients With Bone Metastases, Clinical Genitourinary Cancer, 000(xxx):1-10, (2021).
Nickols, N. et al., aPROMISE: A Novel Automated-PROMISE platform to Standardize Evaluation of Tumor Burden in 18F-DCFPyL (PSMA) images of Veterans with Prostate Cancer, Journal of Nuclear Medicine, 26 pages, May 28, 2021, doi: 10.2967/jnumed.120.261863.
Paschalis, A. et al., Prostate-specific Membrane Antigen Heterogeneity and DNA Repair Defects in Prostate Cancer, European Urology, 76(4):469-478, (2019).

\* cited by examiner

SYSTEMS AND METHODS FOR DEEP-LEARNING-BASED SEGMENTATION OF COMPOSITE IMAGES

CROSS REFERENCE TO RELATED APPLICATIONS

This application is a continuation-in-part of U.S. Non-Provisional application Ser. No. 17/008,404, filed Aug. 31, 2020, which claims priority to and benefit of U.S. Provisional Application No. 63/014,637, filed Apr. 23, 2020, the content of each of which are hereby incorporated by reference in their entirety.

TECHNICAL FIELD

This invention relates generally to systems and methods for creation, analysis, and/or presentation of medical image data. More particularly, in certain embodiments, the invention relates to systems and methods for identifying 3D volumes of interest in medical images.

BACKGROUND

Nuclear medicine imaging involves the use of radiolabeled compounds, referred to as radiopharmaceuticals. Radiopharmaceuticals are administered to patients and accumulate in various regions in the body in manner that depends on, and is therefore indicative of, biophysical and/or biochemical properties of tissue therein, such as those influenced by presence and/or state of disease, such as cancer. For example, certain radiopharmaceuticals, following administration to a patient, accumulate in regions of abnormal osteogenesis associated with malignant bone lesions, which are indicative of metastases. Other radiopharmaceuticals may bind to specific receptors, enzymes, and proteins in the body that are altered during evolution of disease. After administration to a patient, these molecules circulate in the blood until they find their intended target. The bound radiopharmaceutical remains at the site of disease, while the rest of the agent clears from the body.

Nuclear medicine imaging techniques capture images by detecting radiation emitted from the radioactive portion of the radiopharmaceutical. The accumulated radiopharmaceutical serves as a beacon so that an image may be obtained depicting the disease location and concentration using commonly available nuclear medicine modalities. Examples of nuclear medicine imaging modalities include bone scan imaging (also referred to as scintigraphy), single-photon emission computerized tomography (SPECT), and positron emission tomography (PET). Bone scan, SPECT, and PET imaging systems are found in most hospitals throughout the world. Choice of a particular imaging modality depends on and/or dictates the particular radiopharmaceutical used. For example, technetium 99m ($^{99m}$Tc) labeled compounds are compatible with bone scan imaging and SPECT imaging, while PET imaging often uses fluorinated compounds labeled with 18F. The compound $^{99m}$Tc methylenediphosphonate ($^{99m}$Tc MDP) is a popular radiopharmaceutical used for bone scan imaging in order to detect metastatic cancer. Radiolabeled prostate-specific membrane antigen (PSMA) targeting compounds such as $^{99m}$Tc labeled 1404 and PyL™ (also referred to as [18F]DCFPyL) can be used with SPECT and PET imaging, respectively, and offer the potential for highly specific prostate cancer detection.

Accordingly, nuclear medicine imaging is a valuable technique for providing physicians with information that can be used to determine the presence and the extent of disease in a patient. The physician can use this information to provide a recommended course of treatment to the patient and to track the progression of disease.

For example, an oncologist may use nuclear medicine images from a study of a patient as input in her assessment of whether the patient has a particular disease, e.g., prostate cancer, what stage of the disease is evident, what the recommended course of treatment (if any) would be, whether surgical intervention is indicated, and likely prognosis. The oncologist may use a radiologist report in this assessment. A radiologist report is a technical evaluation of the nuclear medicine images prepared by a radiologist for a physician who requested the imaging study and includes, for example, the type of study performed, the clinical history, a comparison between images, the technique used to perform the study, the radiologist's observations and findings, as well as overall impressions and recommendations the radiologist may have based on the imaging study results. A signed radiologist report is sent to the physician ordering the study for the physician's review, followed by a discussion between the physician and patient about the results and recommendations for treatment.

Thus, the process involves having a radiologist perform an imaging study on the patient, analyzing the images obtained, creating a radiologist report, forwarding the report to the requesting physician, having the physician formulate an assessment and treatment recommendation, and having the physician communicate the results, recommendations, and risks to the patient. The process may also involve repeating the imaging study due to inconclusive results, or ordering further tests based on initial results. If an imaging study shows that the patient has a particular disease or condition (e.g., cancer), the physician discusses various treatment options, including surgery, as well as risks of doing nothing or adopting a watchful waiting or active surveillance approach, rather than having surgery.

Accordingly, the process of reviewing and analyzing multiple patient images, over time, plays a critical role in the diagnosis and treatment of cancer. There is a significant need for improved tools that facilitate and improve accuracy of image review and analysis for cancer diagnosis and treatment. Improving the toolkit utilized by physicians, radiologists, and other healthcare professionals in this manner provides for significant improvements in standard of care and patient experience.

SUMMARY OF THE INVENTION

Presented herein are systems and methods that provide for improved 3D segmentation of nuclear medicine images using an artificial intelligence-based deep learning approach. For example, in certain embodiments, the machine learning module receives both an anatomical image (e.g., a CT image) and a functional image (e.g., a PET or SPECT image) as input, and generates, as output, a segmentation mask that identifies one or more particular target tissue regions of interest. The two images are interpreted by the machine learning module as separate channels representative of the same volume, analogous to two color channels (e.g., RGB) of a photographic color image. Following segmentation, additional analysis can be performed (e.g., hotspot detection/risk assessment within the identified region of interest). It has been found that using both an anatomical image and a functional image for the segmentation step leads to more accurate results, as compared to using only the anatomical image for segmentation and, subsequently, using the functional image just for hotspot detection.

As described herein, leveraging information from both the anatomical image and the functional image provides improved segmentation performance, particularly for challenging tissue regions such as the bladder. Other tissue regions, such as prostate, aorta, heart, lungs, and skeletal regions (e.g., various bones) may also be segmented using the approaches described herein.

For example, using both images (anatomical and functional images) for segmentation may be particularly helpful in precisely delineating (in the images) organs with higher uptake of imaging agent (e.g., PyL™), e.g., bladder, liver, spleen, kidneys, prostate, bones, lymph nodes, the aorta, etc. In certain embodiments, information about tracer uptake by a particular organ (or other region) is also used by the machine learning module (e.g., neural network) as input to help it more accurately delineate structures (e.g., adjacent structures) that are similar in the anatomical image.

In certain embodiments, a coarse segmentation is performed, followed by a fine segmentation. In certain embodiments, the coarse segmentation is performed using the anatomical image (e.g., CT image) only, while the fine segmentation is performed using both the anatomical image (e.g., CT image) and the functional image (e.g., PET or SPECT image). In certain embodiments, the coarse segmentation also uses both the anatomical image and the functional image (e.g., like the fine segmentation).

In certain embodiments, the anatomical image and the functional image are obtained at the same time and co-registration is unnecessary. In other embodiments, the anatomical image and the functional image are co-registered prior to performing the segmentation methods described herein. In certain embodiments, one image has lower resolution than the other (e.g., the PET image may have lower resolution than the CT image), e.g., and may have a smaller field-of-view in the inferior-superior direction. In this situation, the lower-resolution image may be resampled to the higher-resolution frame of reference and resolution.

In one aspect, the invention is directed to a method for automatically processing 3D images to identify 3D volumes corresponding to a particular target tissue region [e.g., a soft tissue region (e.g., a particular organ or one or more portions thereof); e.g., a set of one or more bone(s)] within a subject (e.g., a human subject), the method comprising: (a) receiving, by a processor of a computing device, a 3D anatomical image of the subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (b) receiving, by the processor, a 3D functional image of the subject obtained using a functional imaging modality [e.g., positron emission tomography (PET); e.g., single-photon emission computed tomography (SPECT)] [e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (c) automatically generating, by the processor, using a machine learning module, a 3D segmentation mask that identifies, within the 3D anatomical image and/or the 3D functional image, a 3D volume of interest (VOI) corresponding to the target tissue region [e.g., wherein the 3D segmentation mask identifies (e.g., delineates) a boundary of the 3D volume of interest and/or voxels of the 3D anatomical image and/or the 3D functional image falling within (e.g., within the boundary of) the 3D volume of interest; e.g., wherein the 3D segmentation mask distinguishes voxels of the 3D anatomical image corresponding to locations within the target tissue region from other voxels of the 3D anatomical image; e.g., wherein the 3D segmentation mask distinguishes voxels of the 3D functional image corresponding to locations within the target tissue region from other voxels of the 3D functional image], wherein the machine learning module receives at least two channels of input, said input channels comprising a first input channel corresponding to at least a portion of the 3D anatomical image and a second input channel corresponding to at least a portion of the 3D functional image [e.g., wherein the machine learning module receives a PET image and a CT image as separate channels (e.g., separate channels representative of the same volume) (e.g., analogous to receipt by a machine learning module of two color channels (RGB) of a photographic color image)]; and (d) storing and/or providing for display and/or further processing, by the processor, the 3D segmentation mask.

In certain embodiments, the target tissue region comprises a bladder (e.g., urinary bladder) of the subject.

In certain embodiments, the target tissue region comprises a prostate of the subject.

In certain embodiments, the target tissue region comprises one or more skeletal regions (e.g., one or more bones) of the subject.

In certain embodiments, the target tissue region comprises one or more members selected from the group consisting of a liver, a spleen, and (one or both) kidney(s) of the subject.

In certain embodiments, the target tissue region comprises a heart of the subject and/or an aorta or portion thereof.

In certain embodiments, the 3D functional image comprises a PET or SPECT image obtained following administration of an agent (e.g., a radiopharmaceutical; e.g., an imaging agent) to the subject.

In certain embodiments, the agent comprises a PSMA binding agent.

In certain embodiments, the agent comprises [18F] DCFPyL.

In certain embodiments, the agent comprises $^{99m}$Tc.

In certain embodiments, the anatomical image comprises a CT image.

In certain embodiments, the machine learning module implements a neural network [e.g., an artificial neural network (ANN); e.g., a convolutional neural network (CNN)].

In certain embodiments, the machine learning module implements a fully convolutional CNN (e.g., a U-net).

In certain embodiments, the method comprises resampling, by the processor, the 3D functional image to match a resolution of the 3D anatomical image and using, at step (c), a portion of the resampled 3D functional image as the second input channel.

In certain embodiments, step (c) comprises: determining, by the processor, using a preliminary machine learning module (e.g., a coarse segmentation machine learning module, different from a subsequently-used fine segmentation machine learning module), an initial VOI within the 3D anatomical image, the initial VOI corresponding to an anatomical region larger than and containing the target tissue region of interest; using the initial VOI of the 3D anatomical image as the first input channel; and using a sub-volume of the 3D functional image corresponding to the initial VOI as the second input channel.

In certain embodiments, the machine learning module generates, as output, a likelihood map comprising a plurality of voxels, each corresponding to a voxel of the anatomical image and having a likelihood value representing a likelihood that the corresponding anatomical image voxel represents a physical volume within the target tissue region.

In certain embodiments, the method comprises generating the 3D segmentation mask based on the likelihood map.

In certain embodiments, the method comprises: identifying, by the processor, using the 3D segmentation mask, a target VOI within the 3D functional image, the target VOI corresponding to the target tissue region; and determining, by the processor, using intensities of voxels of the 3D functional image within the target VOI, one or more uptake metrics indicative of (e.g., that quantify or represent) a quantity of an agent (e.g., a radiopharmaceutical) within the target tissue region [e.g., and determining, by the processor, a map of the one or more uptake metrics over the target tissue region, e.g., thereby identifying one or more hotspots representative of a location of disease such as cancer (or enhanced likelihood of a location of disease) within the target tissue region].

In certain embodiments, the method comprises determining, by the processor, one or more risk index values using the one or more uptake metrics.

In certain embodiments, at least one of the one or more risk index values is/are indicative of a risk of the subject having or developing a particular cancer (e.g., prostate cancer, lung cancer, liver cancer, brain cancer, breast cancer, etc.).

In certain embodiments, at least one of the one or more risk index values are indicative of a risk of the subject having or developing metastatic cancer.

In certain embodiments, at least one of the one or more risk index values are indicative of a likelihood of the subject having a particular state of cancer.

In another aspect, the invention is directed to a system for automatically processing 3D images to identify 3D volumes corresponding to a particular target tissue region [e.g., a soft tissue region (e.g., a particular organ or one or more portions thereof); e.g., a set of one or more bone(s)] within a subject (e.g., a human subject), the system comprising: a processor of a computing device; and a memory having instructions stored thereon, wherein the instructions, when executed by the processor, cause the processor to: (a) receive a 3D anatomical image of the subject obtained using an anatomical imaging modality [e.g., x-ray computed tomography (CT); e.g., magnetic resonance imaging (MM); e.g., ultrasound], wherein the 3D anatomical image comprises a graphical representation of tissue (e.g., soft-tissue and/or bone) within the subject; (b) receive a 3D functional image of the subject obtained using a functional imaging modality [e.g., positron emission tomography (PET); e.g., single-photon emission computed tomography (SPECT)][e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (c) automatically generate using a machine learning module, a 3D segmentation mask that identifies, within the 3D anatomical image and/or the 3D functional image, a 3D volume of interest (VOI) corresponding to the target tissue region [e.g., wherein the 3D segmentation mask identifies (e.g., delineates) a boundary of the 3D volume of interest and/or voxels of the 3D anatomical image and/or the 3D functional image falling within (e.g., within the boundary of) the 3D volume of interest; e.g., wherein the 3D segmentation mask distinguishes voxels of the 3D anatomical image corresponding to locations within the target tissue region from other voxels of the 3D anatomical image; e.g., wherein the 3D segmentation mask distinguishes voxels of the 3D functional image corresponding to locations within the target tissue region from other voxels of the 3D functional image], wherein the machine learning module receives at least two channels of input, said input channels comprising a first input channel corresponding to at least a portion of the 3D anatomical image and a second input channel corresponding to at least a portion of the 3D functional image [e.g., wherein the machine learning module receives a PET image and a CT image as separate channels (e.g., separate channels representative of the same volume) (e.g., analogous to receipt by a machine learning module of two color channels (RGB) of a photographic color image)]; and (d) store and/or provide for display and/or further processing, the 3D segmentation mask.

In certain embodiments, the target tissue region comprises a bladder of the subject.

In certain embodiments, the target tissue region comprises a prostate of the subject.

In certain embodiments, the target tissue region comprises one or more skeletal regions (e.g., one or more bones) of the subject.

In certain embodiments, the target tissue region comprises one or more members selected from the group consisting of a liver, a spleen, and (one or both) kidney(s) of the subject.

In certain embodiments, the target tissue region comprises a heart of the subject and/or an aorta or portion thereof.

In certain embodiments, the 3D functional image comprises a PET or SPECT image obtained following administration of an agent (e.g., a radiopharmaceutical; e.g., an imaging agent) to the subject.

In certain embodiments, the agent comprises a PSMA binding agent.

In certain embodiments, the agent comprises [18F] DCFPyL.

In certain embodiments, the agent comprises $^{99m}$Tc.

In certain embodiments, the anatomical image comprises a CT image.

In certain embodiments, the machine learning module implements a neural network [e.g., an artificial neural network (ANN); e.g., a convolutional neural network (CNN)]. In certain embodiments, the machine learning module implements a fully convolutional CNN (e.g., a U-net).

In certain embodiments, the instructions cause the processor to resample the 3D functional image to match a resolution of the 3D anatomical image and, at step (c), use a portion of the resampled 3D functional image as the second input channel.

In certain embodiments, at step (c), the instructions cause the processor to: use a preliminary machine learning module (e.g., a coarse segmentation machine learning module, different from a subsequently-used fine segmentation machine learning module), to determine an initial VOI within the 3D anatomical image, the initial VOI corresponding to an anatomical region larger than and containing the target tissue region of interest; use the initial VOI of the 3D anatomical image as the first input channel; and use a sub-volume of the 3D functional image corresponding to the initial VOI as the second input channel.

In certain embodiments, the machine learning module generates, as output, a likelihood map comprising a plurality of voxels, each corresponding to a voxel of the anatomical image and having a likelihood value representing a likelihood that the corresponding anatomical image voxel represents a physical volume within the target tissue region.

In certain embodiments, the instructions cause the processor to generate the 3D segmentation mask based on the likelihood map.

In certain embodiments, the instructions cause the processor to use the 3D segmentation mask to identify a target VOI within the 3D functional image, the target VOI corresponding to the target tissue region; and use intensities of voxels of the 3D functional image within the target VOI to determine one or more uptake metrics indicative of (e.g., that quantify or represent) a quantity of an agent (e.g., a radiopharmaceutical) within the target tissue region [e.g., and determine a map of the one or more uptake metrics over the target tissue region, e.g., thereby identifying one or more hotspots representative of a location of disease such as cancer (or enhanced likelihood of a location of disease) within the target tissue region].

In certain embodiments, the instructions cause the processor to determine one or more risk index values using the one or more uptake metrics.

In certain embodiments, at least one of the one or more risk index values is/are indicative of a risk of the subject having or developing a particular cancer (e.g., prostate cancer, lung cancer, liver cancer, brain cancer, breast cancer, etc.).

In certain embodiments, at least one of the one or more risk index values are indicative of a risk of the subject having or developing metastatic cancer.

In certain embodiments, at least one of the one or more risk index values are indicative of a likelihood of the subject having a particular state of cancer.

Features of embodiments described with respect to one aspect of the invention may be applied with respect to another aspect of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other objects, aspects, features, and advantages of the present disclosure will become more apparent and better understood by referring to the following description taken in conjunction with the accompanying drawings, in which:

FIG. 3A is a CT image of the particular patient, showing a region about a bladder of the patient.

FIG. 3B is a PET image corresponding to the CT image of FIG. 3A.

FIG. 3C an image showing the CT image of FIG. 3A, with a first identified bladder region, determined by a neural network that receives a CT image alone as input, overlaid.

FIG. 3D is an image showing the CT image of FIG. 3A, with a second identified bladder region, determined by a neural network that receives both a CT image and a PET image as input, overlaid.

Figure 1A:
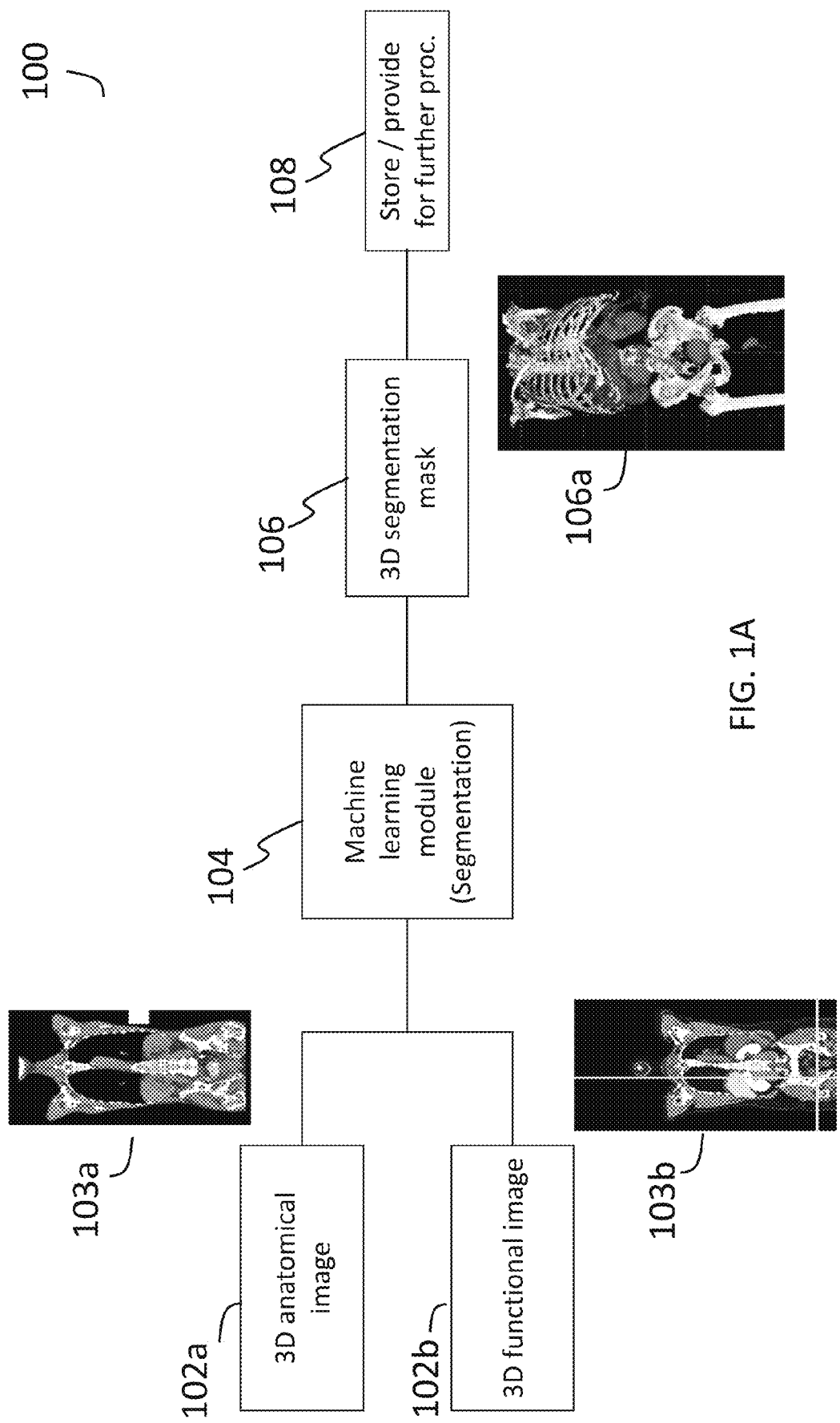
FIG. 1A is a block flow diagram of an example process for deep-learning based composite image segmentation, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are provided for the convenience of the reader—the presence and/or placement of a header is not intended to limit the scope of the subject matter described herein.

A. Nuclear Medicine Images

Nuclear medicine images are obtained using a nuclear imaging modality such as bone scan imaging, Positron Emission Tomography (PET) imaging, and Single-Photon Emission Tomography (SPECT) imaging.

As used herein, an "image"—for example, a 3-D image of mammal—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

As used herein, "3-D" or "three-dimensional" with reference to an "image" means conveying information about three dimensions. A 3-D image may be rendered as a dataset in three dimensions and/or may be displayed as a set of two-dimensional representations, or as a three-dimensional representation.

In certain embodiments, nuclear medicine images use imaging agents comprising radiopharmaceuticals. Nuclear medicine images are obtained following administration of a radiopharmaceutical to a patient (e.g., a human subject), and provide information regarding the distribution of the radiopharmaceutical within the patient. Radiopharmaceuticals are compounds that comprise a radionuclide.

As used herein, "administering" an agent means introducing a substance (e.g., an imaging agent) into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments As used herein, "radionuclide" refers to a moiety comprising a radioactive isotope of at least one element. Exemplary suitable radionuclides include but are not limited to those described herein. In some embodiments, a radionuclide is one used in positron emission tomography (PET). In some embodiments, a radionuclide is one used in single-photon emission computed tomography (SPECT). In some embodiments, a non-limiting list of radionuclides includes $^{99m}$Tc, $^{111}$In, $^{64}$Cu, $^{67}$Ga, $^{68}$Ga, $^{186}$Re, $^{188}$Re, $^{153}$Sm, $^{177}$Lu, $^{67}$Cu, $^{123}$I, $^{124}$I, $^{125}$I, $^{126}$I, $^{131}$I, $^{11}$C, $^{13}$N, $^{15}$O, $^{18}$F, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{105}$Rh, $^{111}$Ag, $^{89}$Zr, $^{225}$Ac, $^{82}$Rb, $^{75}$Br, $^{76}$Br, $^{77}$Br, $^{80}$Br, $^{80m}$Br, $^{82}$Br, $^{83}$Br, $^{211}$At and $^{192}$Ir.

As used herein, the term "radiopharmaceutical" refers to a compound comprising a radionuclide. In certain embodiments, radiopharmaceuticals are used for diagnostic and/or therapeutic purposes. In certain embodiments, radiopharmaceuticals include small molecules that are labeled with one or more radionuclide(s), antibodies that are labeled with one or more radionuclide(s), and antigen-binding portions of antibodies that are labeled with one or more radionuclide(s).

Nuclear medicine images (e.g., PET scans; e.g., SPECT scans; e.g., whole-body bone scans; e.g. composite PET-CT images; e.g., composite SPECT-CT images) detect radiation emitted from the radionuclides of radiopharmaceuticals to form an image. The distribution of a particular radiopharmaceutical within a patient may be determined by biological mechanisms such as blood flow or perfusion, as well as by specific enzymatic or receptor binding interactions. Different radiopharmaceuticals may be designed to take advantage of different biological mechanisms and/or particular specific enzymatic or receptor binding interactions and thus, when administered to a patient, selectively concentrate within particular types of tissue and/or regions within the patient. Greater amounts of radiation are emitted from regions within the patient that have higher concentrations of radiopharmaceutical than other regions, such that these regions appear brighter in nuclear medicine images. Accordingly, intensity variations within a nuclear medicine image can be used to map the distribution of radiopharmaceutical within the patient. This mapped distribution of radiopharmaceutical within the patient can be used to, for example, infer the presence of cancerous tissue within various regions of the patient's body.

For example, upon administration to a patient, technetium 99m methylenediphosphonate ($^{99m}$Tc MDP) selectively accumulates within the skeletal region of the patient, in particular at sites with abnormal osteogenesis associated with malignant bone lesions. The selective concentration of radiopharmaceutical at these sites produces identifiable hotspots—localized regions of high intensity in nuclear medicine images. Accordingly, presence of malignant bone lesions associated with metastatic prostate cancer can be inferred by identifying such hotspots within a whole-body scan of the patient. As described in the following, risk indices that correlate with patient overall survival and other prognostic metrics indicative of disease state, progression, treatment efficacy, and the like, can be computed based on automated analysis of intensity variations in whole-body scans obtained following administration of $^{99m}$Tc MDP to a patient. In certain embodiments, other radiopharmaceuticals can also be used in a similar fashion to $^{99m}$Tc MDP.

In certain embodiments, the particular radiopharmaceutical used depends on the particular nuclear medicine imaging modality used. For example 18F sodium fluoride (NaF) also accumulates in bone lesions, similar to $^{99m}$Tc MDP, but can be used with PET imaging. In certain embodiments, PET imaging may also utilize a radioactive form of the vitamin choline, which is readily absorbed by prostate cancer cells.

In certain embodiments, radiopharmaceuticals that selectively bind to particular proteins or receptors of interest—particularly those whose expression is increased in cancerous tissue may be used. Such proteins or receptors of interest include, but are not limited to tumor antigens, such as CEA, which is expressed in colorectal carcinomas, Her2/neu, which is expressed in multiple cancers, BRCA 1 and BRCA 2, expressed in breast and ovarian cancers; and TRP-1 and -2, expressed in melanoma.

For example, human prostate-specific membrane antigen (PSMA) is upregulated in prostate cancer, including metastatic disease. PSMA is expressed by virtually all prostate cancers and its expression is further increased in poorly differentiated, metastatic and hormone refractory carcinomas. Accordingly, radiopharmaceuticals corresponding to PSMA binding agents (e.g., compounds that a high affinity to PSMA) labelled with one or more radionuclide(s) can be used to obtain nuclear medicine images of a patient from which the presence and/or state of prostate cancer within a variety of regions (e.g., including, but not limited to skeletal regions) of the patient can be assessed. In certain embodiments, nuclear medicine images obtained using PSMA binding agents are used to identify the presence of cancerous tissue within the prostate, when the disease is in a localized state. In certain embodiments, nuclear medicine images obtained using radiopharmaceuticals comprising PSMA binding agents are used to identify the presence of cancerous tissue within a variety of regions that include not only the prostate, but also other organs and tissue regions such as lungs, lymph nodes, and bones, as is relevant when the disease is metastatic.

In particular, upon administration to a patient, radionuclide labelled PSMA binding agents selectively accumulate within cancerous tissue, based on their affinity to PSMA. In a similar manner to that described above with regard to $^{99m}$Tc MDP, the selective concentration of radionuclide labelled PSMA binding agents at particular sites within the patient produces detectable hotspots in nuclear medicine images. As PSMA binding agents concentrate within a variety of cancerous tissues and regions of the body expressing PSMA, localized cancer within a prostate of the patient and/or metastatic cancer in various regions of the patient's body can be detected, and evaluated. Risk indices that correlate with patient overall survival and other prognostic metrics indicative of disease state, progression, treatment efficacy, and the like, can be computed based on automated analysis of intensity variations in nuclear medicine images obtained following administration of a PSMA binding agent radiopharmaceutical to a patient.

A variety of radionuclide labelled PSMA binding agents may be used as radiopharmaceutical imaging agents for nuclear medicine imaging to detect and evaluate prostate cancer. In certain embodiments, the particular radionuclide labelled PSMA binding agent that is used depends on factors such as the particular imaging modality (e.g., PET; e.g., SPECT) and the particular regions (e.g., organs) of the patient to be imaged. For example, certain radionuclide labelled PSMA binding agents are suited for PET imaging, while others are suited for SPECT imaging. For example, certain radionuclide labelled PSMA binding agents facilitate imaging a prostate of the patient, and are used primarily when the disease is localized, while others facilitate imaging organs and regions throughout the patient's body, and are useful for evaluating metastatic prostate cancer.

A variety of PSMA binding agents and radionuclide labelled versions thereof are described in U.S. Pat. Nos. 8,778,305, 8,211,401, and 8,962,799, each of which are incorporated herein by reference in their entireties. Several PSMA binding agents and radionuclide labelled versions thereof are also described in PCT Application PCT/US2017/058418, filed Oct. 26, 2017 (PCT publication WO 2018/081354), the content of which is incorporated herein by reference in its entirety. Section E, below, describes several example PSMA binding agents and radionuclide labelled versions thereof, as well.

B. Deep Learning Based Segmentation of Composite Images Using Multiple Image Input Channels Turning to FIG. 1A, the systems and methods described herein provide tools for segmenting composite images via deep learning techniques, for example using convolutional neural networks. In certain embodiments, composite images comprise an anatomical image, such as a CT image or MRI, and a functional image, such as a PET or SPECT image. In certain embodiments, the anatomical and functional images correspond to similar or overlapping regions of the subject, such that they can be overlaid or co-registered. In this manner, the anatomical image provides anatomical information, such as the physical locations of various organs and specific tissue regions, while the functional image conveys functional information, for example via a map of radiopharmaceutical distribution within the various organs and specific tissue regions. In certain embodiments, image segmentation is performed to identify one or more volumes of interest (VOIs) corresponding to specific target tissue regions (e.g., a prostate, a bladder, a gluteal muscle, a liver, kidneys, an aorta portion, one or more bones, etc.) within the anatomical image of a composite image. The identification of VOIs within the anatomical image can be transferred to the functional image (e.g., co-aligned functional image) of the composite image (e.g., by mapping one or more segmentation masks that identify the VOIs within the anatomical image to the functional image), and used to determine, e.g., in which organs radiopharmaceutical uptake has accumulated.

The approaches described herein offer improved image segmentation by expressly utilizing information from both the anatomical and functional image of a composite image to perform image segmentation. As shown in the example process 100 of FIG. 1, both an anatomical image 102a and a functional image 102b are received, thereby providing a composite image. FIG. 1A shows an example CT image 103a and corresponding PET image (obtained using PyL™ as a radiopharmaceutical) 103b as examples of 3D anatomical and functional images of a composite image (e.g., a PET/CT image). As shown in FIG. 1A, a machine learning module 104 is used to perform image segmentation in order to generate a 3D segmentation mask 106 that identifies one or more target VOIs that correspond to specific tissue regions of interest. In improved process 100, both the 3D anatomical image and the 3D functional image are received as input by the machine learning module 104 and used to perform segmentation. The two images are interpreted by the machine learning module as separate channels representative of the same volume, analogous to two color channels (e.g., RGB) of a photographic color image. In this manner, rather than perform segmentation based solely on, e.g., the 3D anatomical image, the approaches described herein leverage information from both the 3D anatomical image and the 3D functional image. It has been found (see, e.g., section C, below) that using both an anatomical image and a functional image for the segmentation step 104 leads to more accurate results, as compared to using only the anatomical image for segmentation and, subsequently, using the functional image just for hotspot detection. The 3D segmentation mask 106a may identify the target VOIs (e.g., regions such as a bladder) within the 3D anatomical image and/or the 3D functional image Following segmentation, additional analysis can be performed (e.g., hotspot detection/risk assessment within the identified region of interest) 108, e.g., utilizing the anatomical information (e.g., 3D locations and boundaries of particular organs and/or tissue regions of interest, portions thereof) provided by the 3D segmentation mask.

As described herein, leveraging information from both the anatomical image and the functional image provides improved segmentation performance, particularly for challenging tissue regions such as the bladder. Other tissue regions, such as prostate, aorta, heart, lungs, and skeletal regions (e.g., various bones) may also be segmented using the approaches described herein.

Figure 1C:
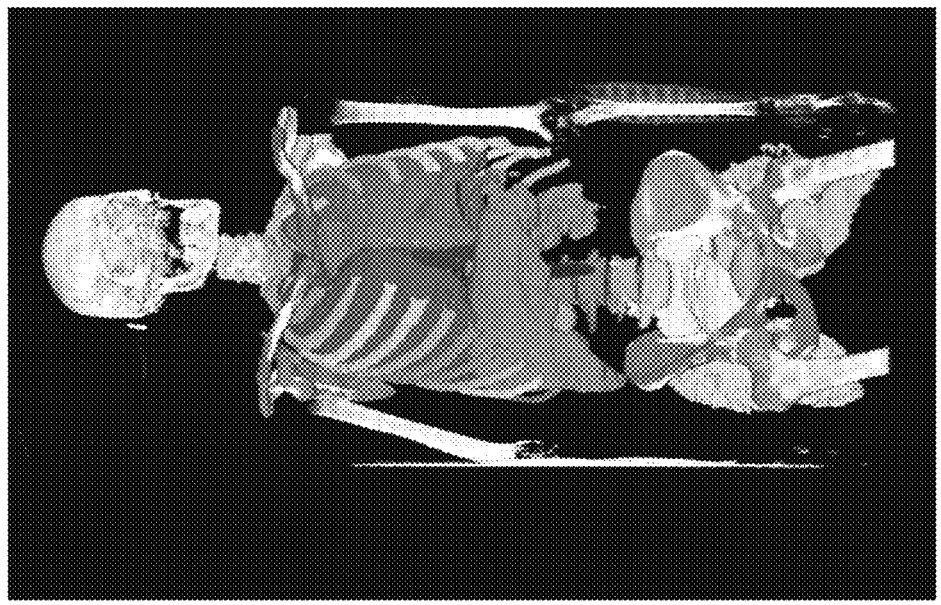
FIG. 1C is an illustrative example showing 3D segmentation masks, according to an illustrative embodiment.
Figure 1B:
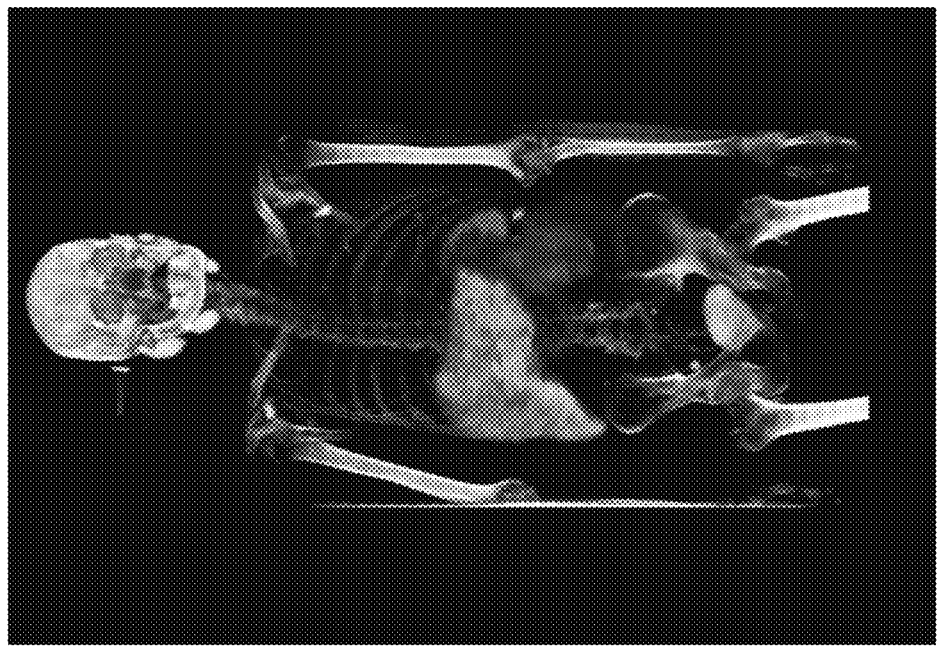
FIG. 1B is an example of a composite PET/CT image, according to an illustrative embodiment.

FIG. 1B shows an example PET/CT image, which may be received as input by a machine learning module in accordance with the approaches described herein. As described herein, the PET image and the CT image may be received as separate channels, analogous to different colors of an RBG image, by the machine learning module. FIG. 1C shows an illustrative example of a plurality of 3D segmentation masks identifying various organs and tissue regions, including a bladder, as well as other regions (e.g., a 3D segmentation map comprising a plurality of segmentation masks). For example, segmentation masks may identify one or more of bones and/or soft tissue regions such as one or more of the following: a clavicle, a femur, a fibula, a hip bone, a humerus, a mandible, a patella, a radius, a tibia, an ulna, one or more ribs a sacrum and coccyx, a scapula, a skull, a sternum, a vertebrae region, and an individual vertebra. In certain embodiments, segmentation mask identify one or more of the following soft tissue regions: an adrenal gland, an aorta or portion thereof (e.g., a thoracic portion; e.g., an abdominal portion), a brain, a bronchi, a gallbladder, a gluteus maximus, a heart, a common iliac artery, a kidney, a liver, a lung, a pancreas, a prostate, a rectum, a spleen, a trachea, a urinary bladder, a ventricle, and a parotid gland.

In certain embodiments, the segmentation approaches described herein may utilize and/or be combined with features of other segmentation techniques, such as those described in PCT/US2019/012486, filed Jan. 7, 2019 (PCT publication WO 2019/136349) and PCT/EP2020/050132, filed Jan. 6, 2020 (PCT publication WO 2020/144134), the contents of which are hereby incorporated by reference in their entirety. For example, the approach described herein whereby both an anatomical and functional image are as input to a machine learning module for image segmentation may be used in combination with the two-step "bounding box" approach described in PCT/US2019/012486 and PCT/EP2020/050132, e.g., to perform an initial coarse segmentation to identify an initial volume of interest (e.g., corresponding to a general anatomical region, such as a pelvic region) and/or to identify one or more specific target VOIs therein (e.g., corresponding to particular target tissue regions of interest, such as a prostate region, bladder region, liver region, etc.). Segmentation masks generated via the approaches described herein may be utilized for whole body image segmentation, for example as described in PCT/EP2020/050132, as well as input (e.g., to provide anatomical context) for hotspot detection approaches, such as those described in PCT/EP2020/050132. In certain embodiments, the systems and methods described herein may be implemented in a cloud-based platform, for example as described in PCT/US2017/058418, filed Oct. 26, 2017 (PCT publication WO 2018/081354), the content of which is hereby incorporated by reference in its entirety.

C. Deep Learning Based Urinary Bladder Segmentation using PSMA PET/CT Images

Organ segmentation is an important but time-consuming step in the clinical workflow, both when diagnosing and treating patients with prostate cancer. Deep learning methods can be implemented to alleviate this problem, e.g., based on CT or MRI images.

When considering segmentation of the urinary bladder in prostate cancer patients, there may be multiple factors that make the delineation difficult. For example, the patient may have had a prostatectomy or have a catheter, both of which could change the anatomy and position of the urinary bladder, or the patient may have a hip replacement creating image artifacts in the CT image.

When acquiring PET/CT images, the PET tracer accumulates in the urinary bladder, making it clearly visible. The bladder may be segmented using the PET image only. However, there may be lesions in the prostate gland or in nearby lymph nodes with high tracer uptake which might then erroneously be segmented as urinary bladder.

In this example, a deep learning based method is evaluated that takes both PET and CT images as input to segment the urinary bladder.

Figure 2:
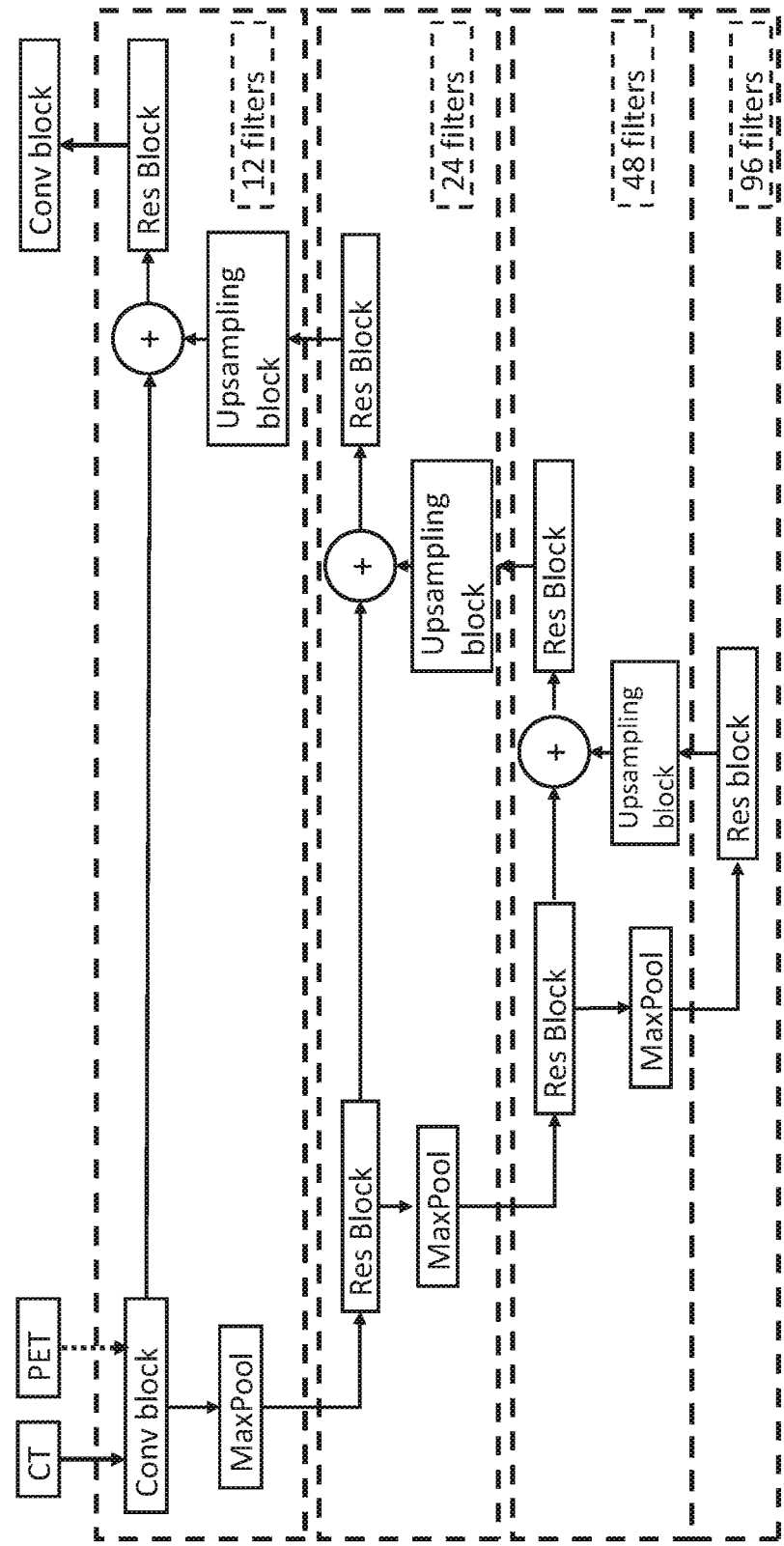
FIG. 2 is a block diagram of an exemplary structure of a neural network used for performing segmentation of composite images, according to an illustrative embodiment.

Materials and Methods: A data set containing 39 pairs of PSMA PET/CT images and manually crafted urinary bladder segmentations were used to train and evaluate the deep learning segmentation. The network was trained on 31 images and evaluated on 8 images. Cross-validation was performed such that the evaluation set was rotated, and the network re-trained until evaluation was performed on all 39 images. The Sørensen-Dice score was used to evaluate the performance of the segmentation. Two sets of u-net neural network structures were trained (Ronneberger et al., 2015), one which only received the CT image, and one which took both the CT and the PET image as input. The two inputs in the latter case can be interpreted as two color-channels in the neural network. FIG. 2 shows a schematic of the neural network structure 200 used to perform segmentation using both the CT and the PET images as input.

Results: Evaluated on all images, the network using only low-dose CT as input achieved a mean Dice score of 0.73 with a standard deviation of 0.20. The network receiving the PET/CT image pair as input achieved a Dice score of 0.76 with a standard deviation of 0.14.

While use of CT images alone can provide accurate segmentation of the bladder, in certain cases use of the PET image along with the CT image provides a significant advantage in terms of segmentation accuracy. Accordingly, the network using the PET/CT image pair as input provided both a higher mean and a lower standard deviation.

Figure 3B:
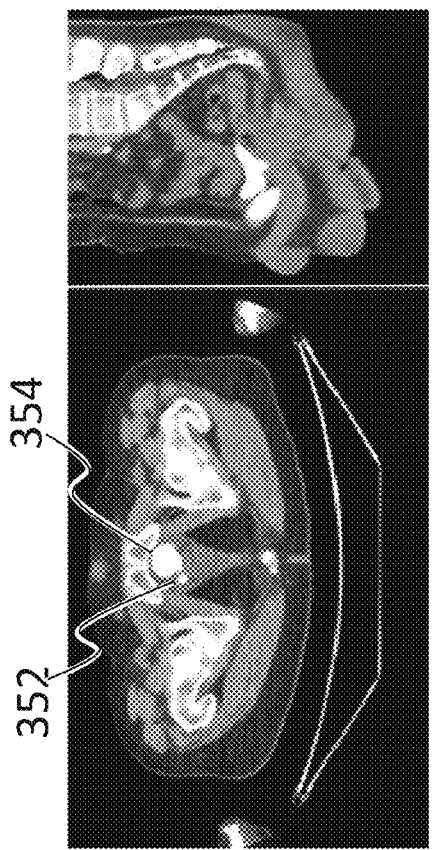
FIGS. 3A-3D are a set of four images of a particular patient, showing CT and PET images and comparing bladder segmentation results obtained using the CT image alone with results obtained using the CT/PET image pair (e.g., both the CT and PET images), according to an illustrative embodiment.
Figure 3D:
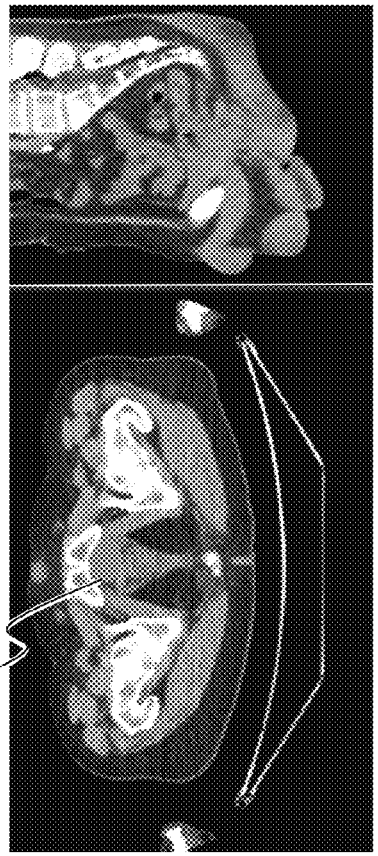
Figure 3A:
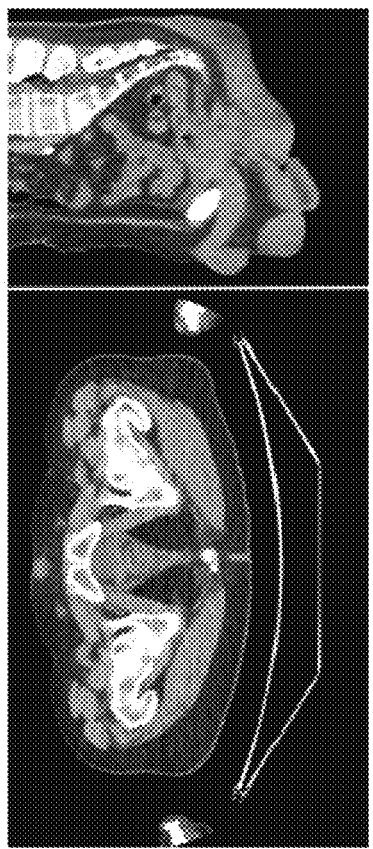
Figure 3C:
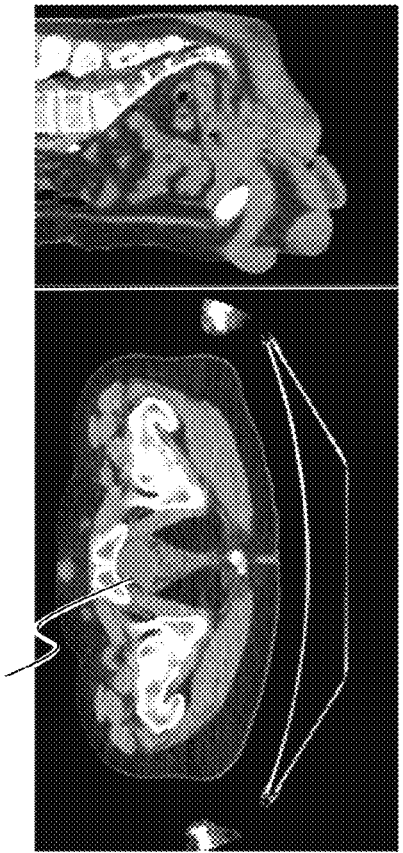

One such example where use of both the PET and CT image as input to the network for segmentation provided a significant advantage over use of the CT image alone is shown in FIGS. 3A-D. FIGS. 3A-D show four images, each showing a transverse (left portion of each image) and a sagittal plane (right portion of each image) of a same patient. The patient has a prostate tumor close to their bladder. FIG. 3A shows a CT image of the patient. The tumor is difficult to observe and distinguish from the bladder in the CT image of FIG. 3A. In the PET image, shown in FIG. 3B, however, the region of the image corresponding to the tumor 352 can readily be distinguished from the bladder region 354. FIGS. 3C and 3D compare segmentation results the two different segmentation approaches. FIG. 3C shows a first bladder region as determined by the network that used the CT image alone as input, 362 (red region in FIG. 3C), overlaid on the CT image. FIG. 3D shows a second bladder region as determined by the network that used both the CT and the PET image, 364 (red region in FIG. 3D), overlaid on the CT image. Comparing FIGS. 3C and 3D, it can be seen that the first bladder region 362 appears to encompass the tumor region as well, while the second bladder region 364, identified by the network that used the PET image in addition to the CT image, does not include this tumor region. The Dice score for the bladder segmentation performed using just the CT image alone, without the PET image, was 0.64, while a significantly improved Dice score, 0.74, was obtained for the bladder segmentation that used both the PET image and the CT image.

Conclusions: By utilizing both the PET and the CT image as input to a deep-learning based semantic segmentation, improved results are seen.

D. Automated Lesion Detection in and Quantification of PyL™ PET/CT via Deep Learning Comprehensive and automated quantification of PyL™-PSMA PET/CT findings may be of great value in routine clinical practice as well as in clinical trials. Described here an image analysis tool for automated, structured, and quantitative reporting of PET/CT findings. The image analysis tool automates the process of lesion identification and Standard Uptake Values (SUVs) quantification. It may improve consistency of both inter- and intra-physician PSMA PET/CT assessments of disease.

Methods: The image analysis tool described herein creates a deep-learning based semantic segmentation of the CT image. The segmentation is transferred to the PET image where reference SUVs for liver and aorta blood pool are calculated. Suspicious hotspots, i.e., regions with high uptake in the PET image that may be consistent with disease, are identified and their volumes outlined. For each identified hotspot a range of quantitative measurements are generated, e.g., SUV max and lesion volume, as well as the miPSMA index. Finally, a structured report is generated, summarizing the study data of the patient, together with a detailed list of detected lesions and their respective quantitative measurements. For development of the hotspot detection and delineation algorithm, a data set comprised of 266 PyL-PSMA PET/CT scans with manually annotated lesions was used. Evaluation of reference value computation was performed on 86 independent PyL-PSMA PET/CT images.

Results: A detection sensitivity of 94%, 95% and 94% was achieved for bone, lymph and prostate lesions, respectively. For reference value evaluation, 3 manual readers estimated the liver and aorta blood reference values. The Pearson correlation coefficient between reader-generated reference values were in the range 0.73-0.78 for blood pool and 0.78-0.97 for liver. The correlation between the software and reader generated reference values were in the range 0.82-0.88 for blood pool and 0.81-0.95 for liver. The standard deviation of manually generated reference values were 0.24 and 1.29 for blood pool and liver, respectively, whereas the reference values generated using the automated image analysis tool of the present example had a standard deviation 0.21 and 1.15.

Conclusions: Automation detection and delineation of lesions using the image analysis tool of the present example demonstrated better consistency than the manual readers.

E. Imaging Agents i. PET Imaging Radionuclide Labelled PSMA Binding Agents

In certain embodiments, the radionuclide labelled PSMA binding agent is a radionuclide labelled PSMA binding agent appropriate for PET imaging.

In certain embodiments, the radionuclide labelled PSMA binding agent comprises [18F]DCFPyL (also referred to as PyL™; also referred to as DCFPyL-18F):

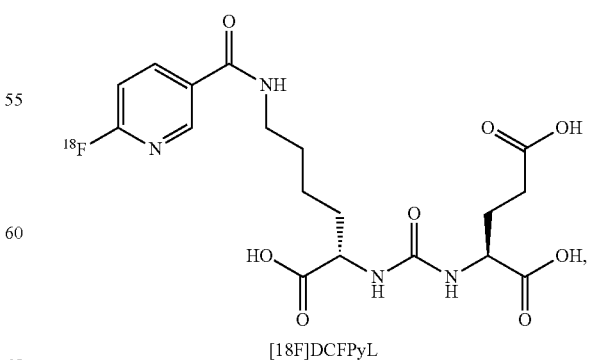

[18F]DCFPyL or a pharmaceutically acceptable salt thereof.

In certain embodiments, the radionuclide labelled PSMA binding agent comprises [18F]DCFBC:
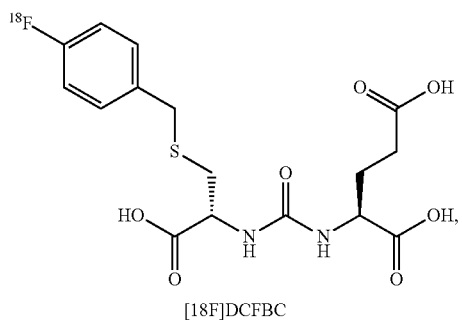 [SMILES: O=C(O)CC[C@H](NC(=O)N[C@@H](CSCc1ccc([18F])cc1)C(=O)O)C(=O)O]
[18F]DCFBC
or a pharmaceutically acceptable salt thereof.
In certain embodiments, the radionuclide labelled PSMA binding agent comprises $^{68}$Ga-PSMA-HBED-CC (also referred to as $^{68}$Ga-PSMA-11):
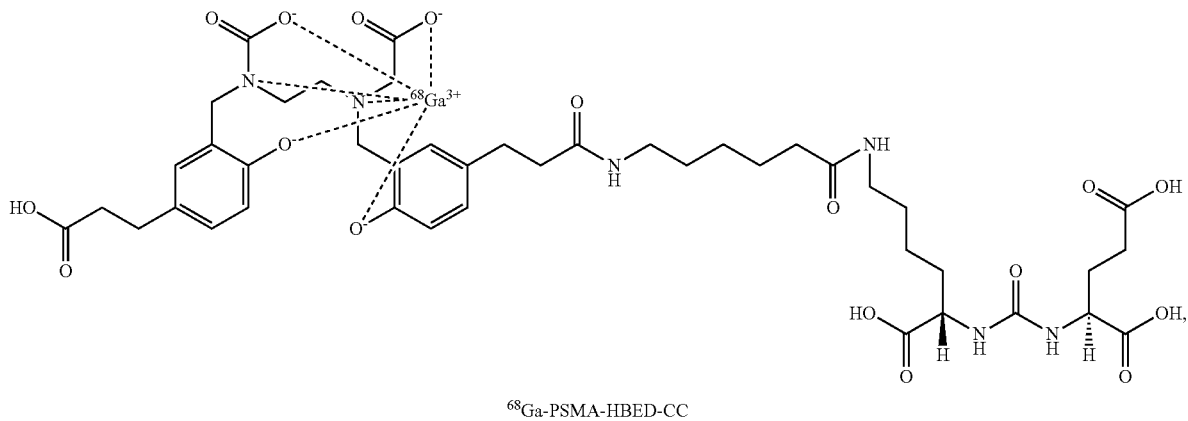
$^{68}$Ga-PSMA-HBED-CC
or a pharmaceutically acceptable salt thereof.

In certain embodiments, the radionuclide labelled PSMA binding agent comprises PSMA-617:

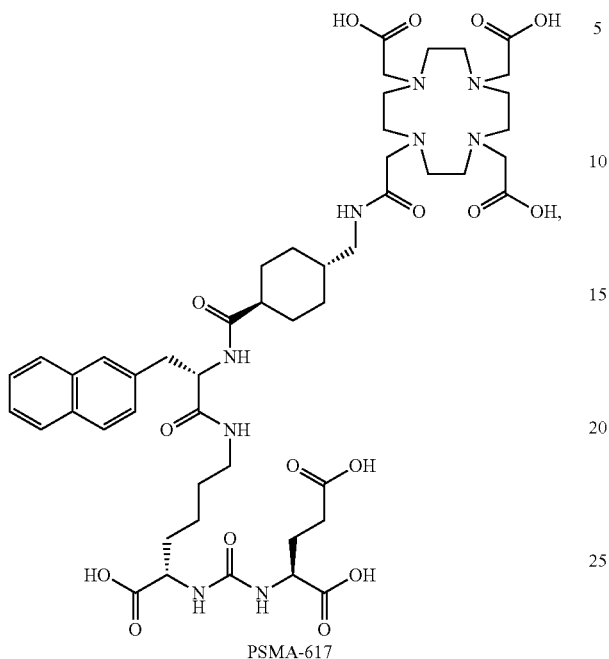

PSMA-617 or a pharmaceutically acceptable salt thereof. In certain embodiments, the radionuclide labelled PSMA binding agent comprises $^{68}$Ga-PSMA-617, which is PSMA-617 labelled with $^{68}$Ga, or a pharmaceutically acceptable salt thereof. In certain embodiments, the radionuclide labelled PSMA binding agent comprises $^{177}$Lu-PSMA-617, which is PSMA-617 labelled with $^{177}$Lu, or a pharmaceutically acceptable salt thereof.

In certain embodiments, the radionuclide labelled PSMA binding agent comprises PSMA-I&T:

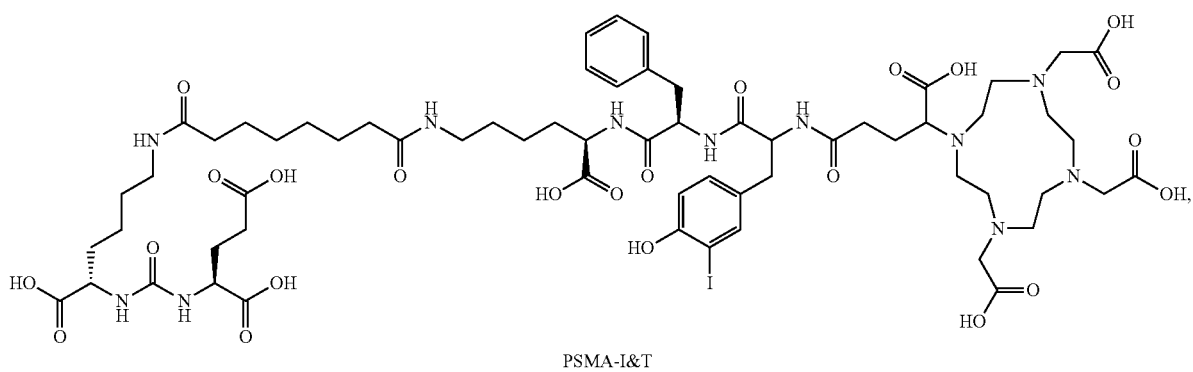 [SMILES: O=C(O)CC[C@H](NC(=O)N[C@@H](CCCCNC(=O)CCCCCCC(=O)NCCCC[C@@H](NC(=O)[C@@H](Cc1ccccc1)NC(=O)C(Cc1ccc(O)c(I)c1)NC(=O)CCC(C(=O)O)N1CCN(CC(=O)O)CCN(CC(=O)O)CCN(CC(=O)O)CC1)C(=O)O)C(=O)O)C(=O)O]

PSMA-I&T or a pharmaceutically acceptable salt thereof. In certain embodiments, the radionuclide labelled PSMA binding agent comprises $^{68}$Ga-PSMA-I&T, which is PSMA-I&T labelled with $^{68}$Ga, or a pharmaceutically acceptable salt thereof.
In certain embodiments, the radionuclide labelled PSMA binding agent comprises PSMA-1007:
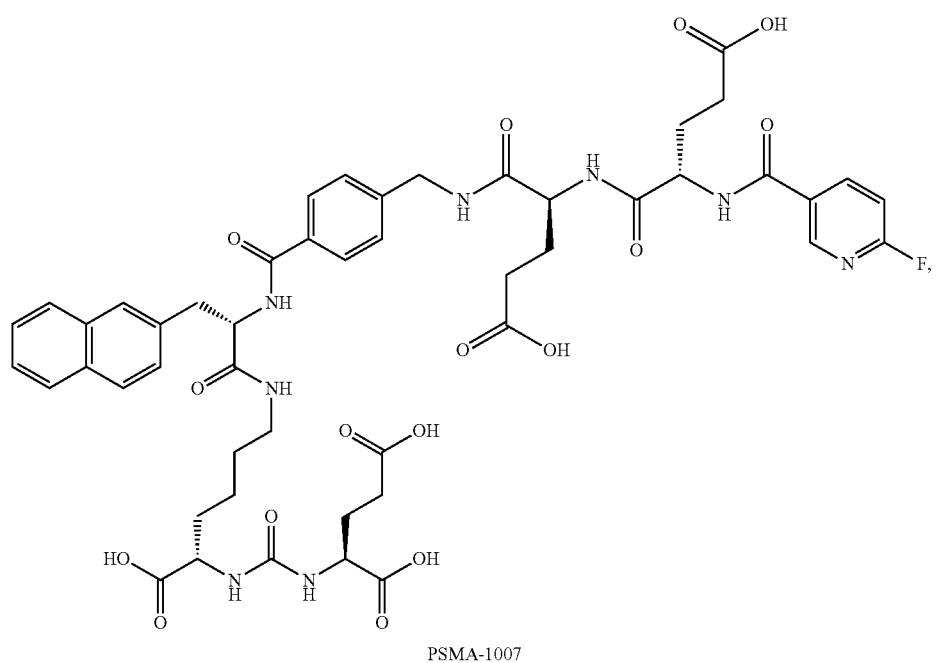
PSMA-1007 or a pharmaceutically acceptable salt thereof. In certain embodiments, the radionuclide labelled PSMA binding agent comprises $^{18}$F-PSMA-1007, which is PSMA-1007 labelled with $^{18}$F, or a pharmaceutically acceptable salt thereof.

ii. SPECT Imaging Radionuclide Labelled PSMA Binding Agents

In certain embodiments, the radionuclide labelled PSMA binding agent is a radionuclide labelled PSMA binding agent appropriate for SPECT imaging.

In certain embodiments, the radionuclide labelled PSMA binding agent comprises 1404 (also referred to as MIP-1404):

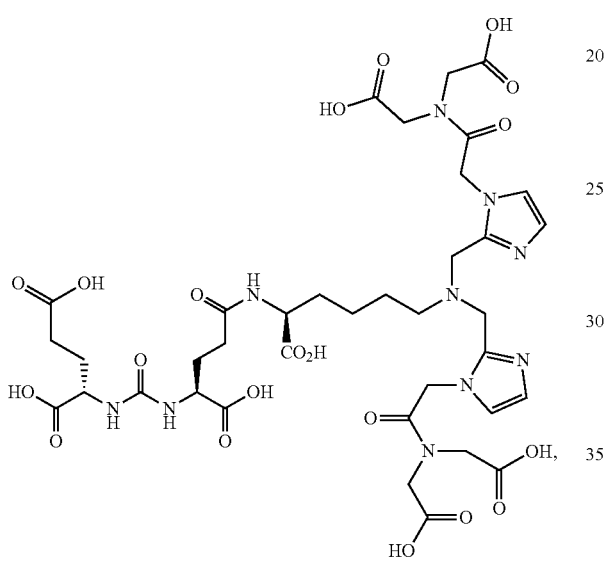

1404 or a pharmaceutically acceptable salt thereof.

In certain embodiments, the radionuclide labelled PSMA binding agent comprises 1405 (also referred to as MIP-1405):

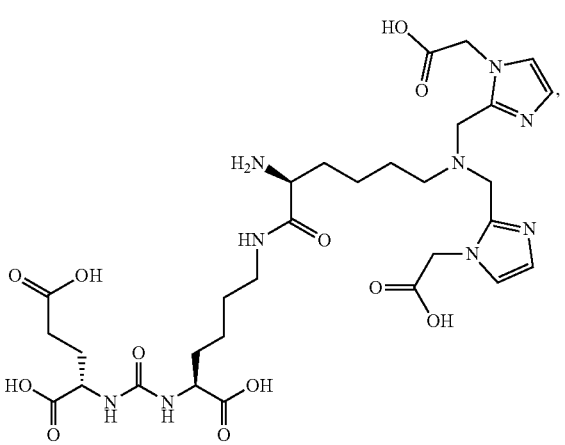

1405 or a pharmaceutically acceptable salt thereof.

In certain embodiments, the radionuclide labelled PSMA binding agent comprises 1427 (also referred to as MIP-1427):

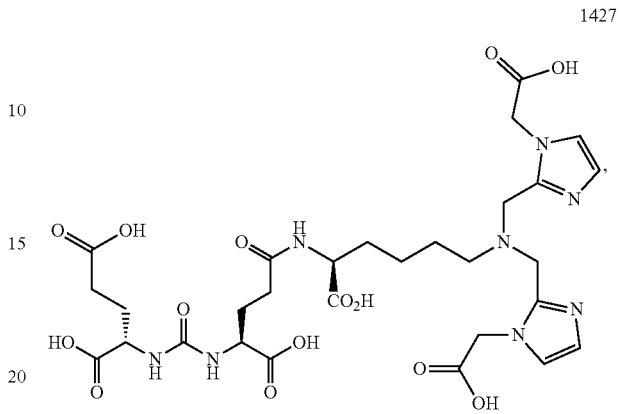

1427 or a pharmaceutically acceptable salt thereof.

In certain embodiments, the radionuclide labelled PSMA binding agent comprises 1428 (also referred to as MIP-1428):

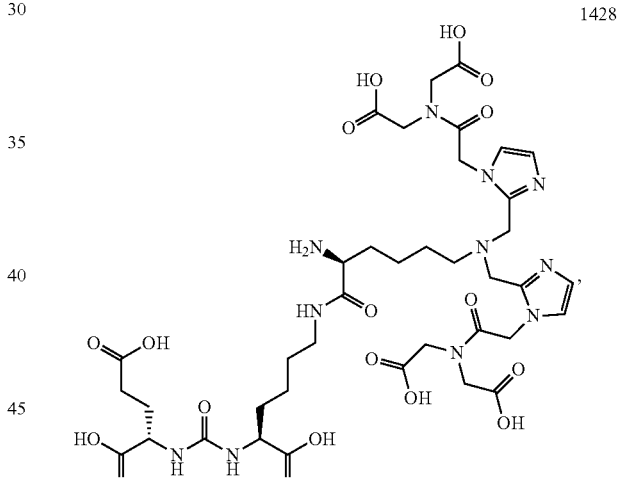

1428 or a pharmaceutically acceptable salt thereof.

In certain embodiments, the PSMA binding agent is labelled with a radionuclide by chelating it to a radioisotope of a metal [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu) (e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)].

In certain embodiments, 1404 is labelled with a radionuclide (e.g., chelated to a radioisotope of a metal). In certain embodiments, the radionuclide labelled PSMA binding agent comprises $^{99m}$Tc-MIP-1404, which is 1404 labelled with (e.g., chelated to) $^{99m}$Tc:

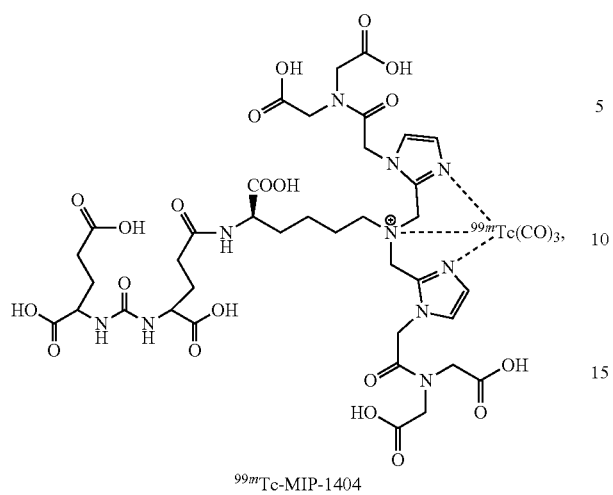

$^{99m}$Tc-MIP-1404 or a pharmaceutically acceptable salt thereof. In certain embodiments, 1404 may be chelated to other metal radioisotopes [e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu) (e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-1404, with the other metal radioisotope substituted for $^{99m}$Tc.

In certain embodiments, 1405 is labelled with a radionuclide (e.g., chelated to a radioisotope of a metal). In certain embodiments, the radionuclide labelled PSMA binding agent comprises $^{99m}$Tc-MIP-1405, which is 1405 labelled with (e.g., chelated to) $^{99m}$Tc:

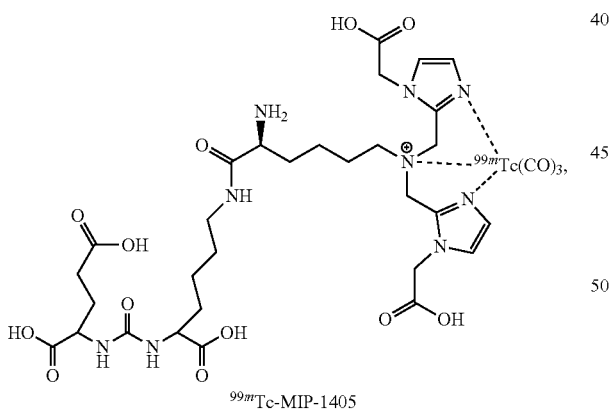

$^{99m}$Tc-MIP-1405 or a pharmaceutically acceptable salt thereof. In certain embodiments, 1405 may be chelated to other metal radioisotopes [e.g., a radioisotope of rhenium (Re) (e.g., rhenium-188 ($^{188}$Re); e.g., rhenium-186 e.g., ($^{186}$Re)); e.g., a radioisotope of yttrium (Y) (e.g., $^{90}$Y); e.g., a radioisotope of lutetium (Lu) (e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-1405, with the other metal radioisotope substituted for $^{99m}$Tc.

In certain embodiments, 1427 is labelled with (e.g., chelated to) a radioisotope of a metal, to form a compound according to the formula below:

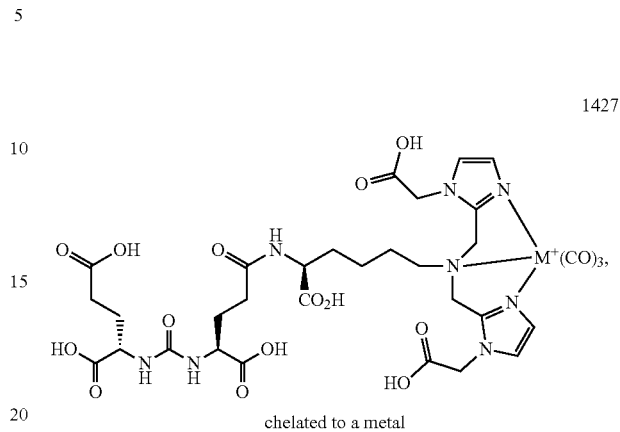

1427 chelated to a metal or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu) (e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] with which 1427 is labelled.

In certain embodiments, 1428 is labelled with (e.g., chelated to) a radioisotope of a metal, to form a compound according to the formula below:

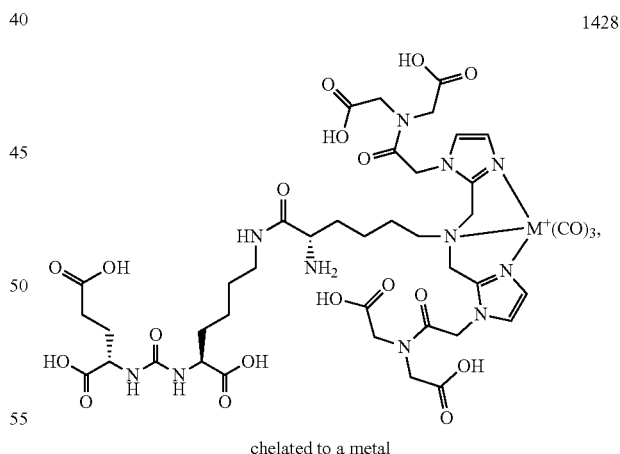

1428 chelated to a metal or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu) (e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] with which 1428 is labelled.

In certain embodiments, the radionuclide labelled PSMA binding agent comprises PSMA I&S:

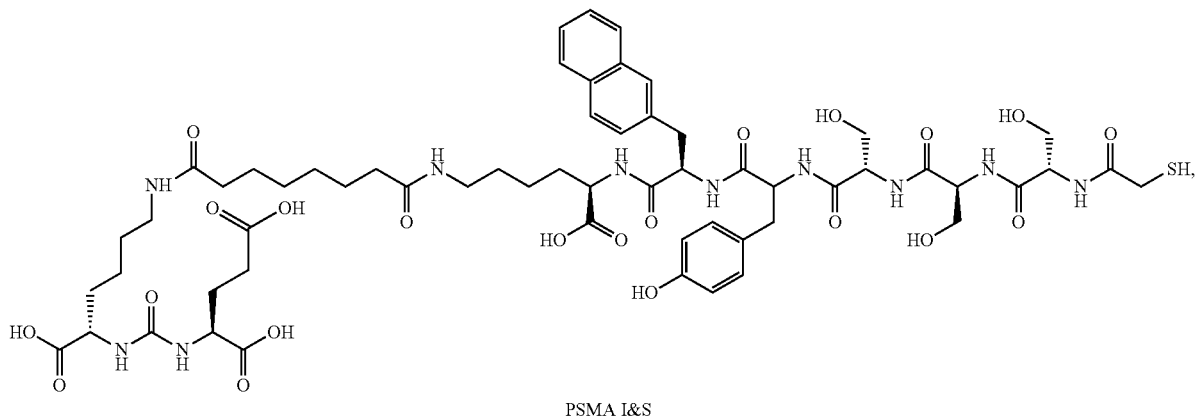 [SMILES: O=C(O)CC[C@H](NC(=O)N[C@@H](CCCCNC(=O)CCCCCCC(=O)NCCCC[C@@H](NC(=O)[C@@H](Cc1ccc2ccccc2c1)NC(=O)C(Cc1ccc(O)cc1)NC(=O)[C@H](CO)NC(=O)[C@H](CO)NC(=O)[C@H](CO)NC(=O)CS)C(=O)O)C(=O)O)C(=O)O]

PSMA I&S or a pharmaceutically acceptable salt thereof. In certain embodiments, the radionuclide labelled PSMA binding agent comprises $^{99m}$Tc-PSMA I&S, which is PSMA I&S labelled with $^{99m}$Tc, or a pharmaceutically acceptable salt thereof.

F. Computer System and Network Architecture

Figure 4:
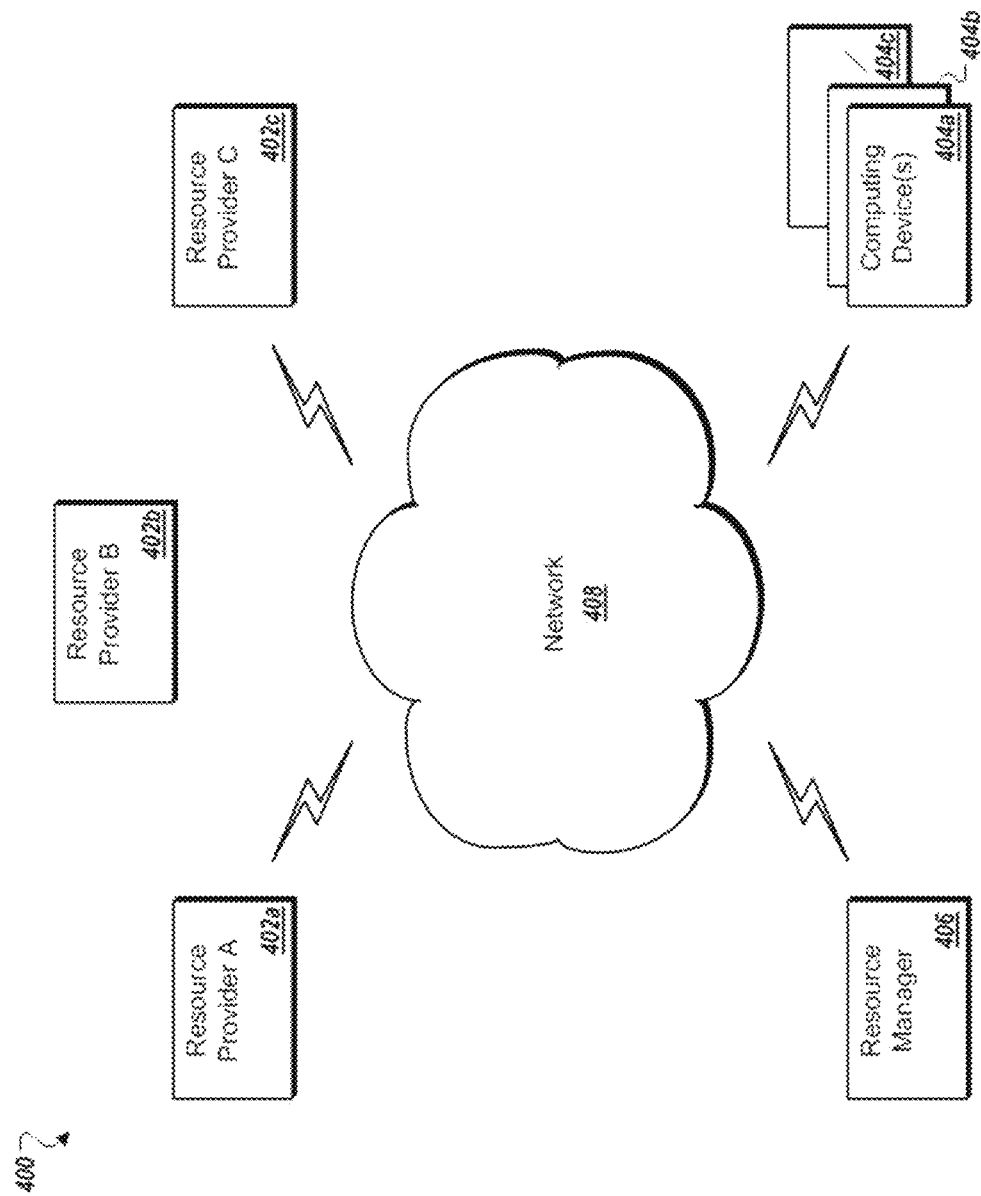
FIG. 4 is a block diagram of an exemplary cloud computing environment, used in certain embodiments.

As shown in FIG. 4, an implementation of a network environment 400 for use in providing systems, methods, and architectures described herein is shown and described. In brief overview, referring now to FIG. 4, a block diagram of an exemplary cloud computing environment 400 is shown and described. The cloud computing environment 400 may include one or more resource providers 402a, 402b, 402c (collectively, 402). Each resource provider 402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 402 may be connected to any other resource provider 402 in the cloud computing environment 400. In some implementations, the resource providers 402 may be connected over a computer network 408. Each resource provider 402 may be connected to one or more computing device 404a, 404b, 404c (collectively, 404), over the computer network 408.

The cloud computing environment 400 may include a resource manager 406. The resource manager 406 may be connected to the resource providers 402 and the computing devices 404 over the computer network 408. In some implementations, the resource manager 406 may facilitate the provision of computing resources by one or more resource providers 402 to one or more computing devices 404. The resource manager 406 may receive a request for a computing resource from a particular computing device 404. The resource manager 406 may identify one or more resource providers 402 capable of providing the computing resource requested by the computing device 404. The resource manager 406 may select a resource provider 402 to provide the computing resource. The resource manager 406 may facilitate a connection between the resource provider 402 and a particular computing device 404. In some implementations, the resource manager 406 may establish a connection between a particular resource provider 402 and a particular computing device 404. In some implementations, the resource manager 406 may redirect a particular computing device 404 to a particular resource provider 402 with the requested computing resource.

Figure 5:
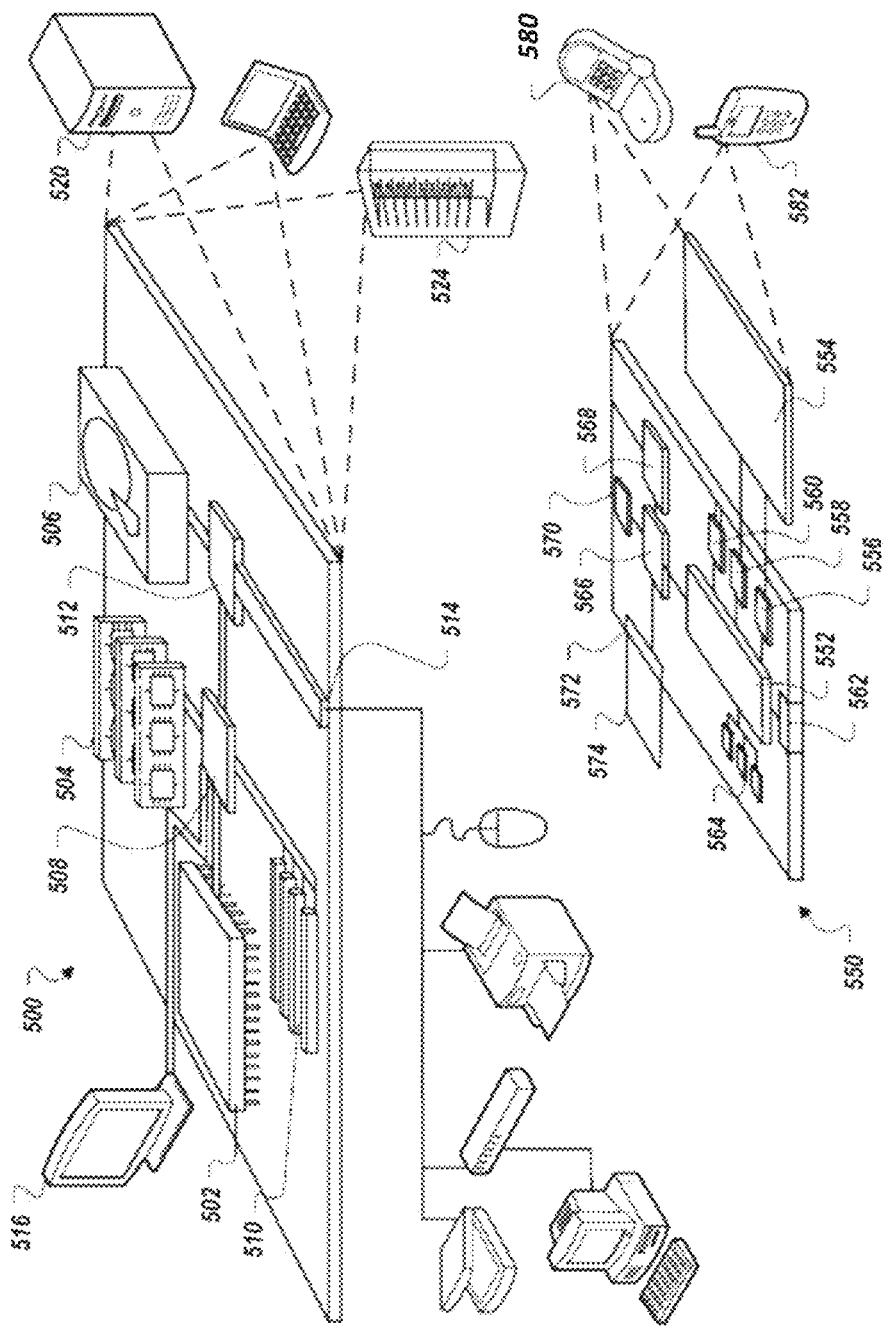
FIG. 5 is a block diagram of an example computing device and an example mobile computing device used in certain embodiments.

FIG. 5 shows an example of a computing device 500 and a mobile computing device 550 that can be used to implement the techniques described in this disclosure. The computing device 500 is intended to represent various forms of digital computers, such as laptops, desktops, workstations, personal digital assistants, servers, blade servers, mainframes, and other appropriate computers. The mobile computing device 550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 500 includes a processor 502, a memory 504, a storage device 506, a high-speed interface 508 connecting to the memory 504 and multiple high-speed expansion ports 510, and a low-speed interface 512 connecting to a low-speed expansion port 514 and the storage device 506. Each of the processor 502, the memory 504, the storage device 506, the high-speed interface 508, the high-speed expansion ports 510, and the low-speed interface 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as a display 516 coupled to the high-speed interface 508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 504 stores information within the computing device 500. In some implementations, the memory 504 is a volatile memory unit or units. In some implementations, the memory 504 is a non-volatile memory unit or units. The memory 504 may also be another form of computer-readable medium, such as a magnetic or optical disk.

The storage device 506 is capable of providing mass storage for the computing device 500. In some implementations, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 502), perform one or more methods, such as those described above. The instructions can also be stored by one or more storage devices such as computer- or machine-readable mediums (for example, the memory 504, the storage device 506, or memory on the processor 502).

The high-speed interface 508 manages bandwidth-intensive operations for the computing device 500, while the low-speed interface 512 manages lower bandwidth-intensive operations. Such allocation of functions is an example only. In some implementations, the high-speed interface 508 is coupled to the memory 504, the display 516 (e.g., through a graphics processor or accelerator), and to the high-speed expansion ports 510, which may accept various expansion cards (not shown). In the implementation, the low-speed interface 512 is coupled to the storage device 506 and the low-speed expansion port 514. The low-speed expansion port 514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 500 may be combined with other components in a mobile device (not shown), such as a mobile computing device 550. Each of such devices may contain one or more of the computing device 500 and the mobile computing device 550, and an entire system may be made up of multiple computing devices communicating with each other.

The mobile computing device 550 includes a processor 552, a memory 564, an input/output device such as a display 554, a communication interface 566, and a transceiver 568, among other components. The mobile computing device 550 may also be provided with a storage device, such as a micro-drive or other device, to provide additional storage. Each of the processor 552, the memory 564, the display 554, the communication interface 566, and the transceiver 568, are interconnected using various buses, and several of the components may be mounted on a common motherboard or in other manners as appropriate.

The processor 552 can execute instructions within the mobile computing device 550, including instructions stored in the memory 564. The processor 552 may be implemented as a chipset of chips that include separate and multiple analog and digital processors. The processor 552 may provide, for example, for coordination of the other components of the mobile computing device 550, such as control of user interfaces, applications run by the mobile computing device 550, and wireless communication by the mobile computing device 550.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 550 with other devices. The external interface 562 may provide, for example, for wired communication in some implementations, or for wireless communication in other implementations, and multiple interfaces may also be used.

The memory 564 stores information within the mobile computing device 550. The memory 564 can be implemented as one or more of a computer-readable medium or media, a volatile memory unit or units, or a non-volatile memory unit or units. An expansion memory 574 may also be provided and connected to the mobile computing device 550 through an expansion interface 572, which may include, for example, a SIMM (Single In Line Memory Module) card interface. The expansion memory 574 may provide extra storage space for the mobile computing device 550, or may also store applications or other information for the mobile computing device 550. Specifically, the expansion memory 574 may include instructions to carry out or supplement the processes described above, and may include secure information also. Thus, for example, the expansion memory 574 may be provide as a security module for the mobile computing device 550, and may be programmed with instructions that permit secure use of the mobile computing device 550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562.

The mobile computing device 550 may communicate wirelessly through the communication interface 566, which may include digital signal processing circuitry where necessary. The communication interface 566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 568 using a radio-frequency. In addition, short-range communication may occur, such as using a Bluetooth®, Wi-Fi™, or other such transceiver (not shown). In addition, a GPS (Global Positioning System) receiver module 570 may provide additional navigation- and location-related wireless data to the mobile computing device 550, which may be used as appropriate by applications running on the mobile computing device 550.

The mobile computing device 550 may also communicate audibly using an audio codec 560, which may receive spoken information from a user and convert it to usable digital information. The audio codec 560 may likewise generate audible sound for a user, such as through a speaker, e.g., in a handset of the mobile computing device 550. Such sound may include sound from voice telephone calls, may include recorded sound (e.g., voice messages, music files, etc.) and may also include sound generated by applications operating on the mobile computing device 550.

The mobile computing device 550 may be implemented in a number of different forms, as shown in the figure. For example, it may be implemented as a cellular telephone 580. It may also be implemented as part of a smart-phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the various modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for automatically processing 3D images to identify 3D volumes corresponding to a particular target tissue region within a subject, the method comprising:
   (a) receiving, by a processor of a computing device, a 3D anatomical image of the subject obtained using an anatomical imaging modality, wherein the 3D anatomical image comprises a graphical representation of tissue within the subject;
(b) receiving, by the processor, a 3D functional image of the subject obtained using a functional imaging modality;
(c) automatically generating, by the processor, using a machine learning module, a 3D segmentation mask that identifies, within the 3D anatomical image and/or the 3D functional image, a 3D volume of interest (VOI) corresponding to the target tissue region,
wherein the machine learning module: (i) receives at least two channels of input, said input channels comprising a first input channel corresponding to at least a portion of the 3D anatomical image and a second input channel corresponding to at least a portion of the 3D functional image and (ii) utilizes both the portion of the 3D anatomical image and the portion of the 3D functional image to perform image segmentation; and
(d) storing and/or providing, for display and/or further processing, by the processor, the 3D segmentation mask.

2. The method of claim 1, wherein the target tissue region comprises a bladder of the subject.

3. The method of claim 1, wherein the target tissue region comprises a prostate of the subject.

4. The method of claim 1, wherein the target tissue region comprises one or more skeletal regions of the subject.

5. The method of claim 1, wherein the target tissue region comprises one or more members selected from the group consisting of a liver, a spleen, and kidney(s) of the subject.

6. The method of claim 1, wherein the target tissue region comprises a heart of the subject and/or an aorta or portion thereof.

7. The method of claim 1, wherein the 3D functional image comprises a PET or SPECT image obtained following administration of an agent to the subject.

8. The method of claim 7, wherein the agent comprises a PSMA binding agent.

9. The method of claim 8, wherein the agent comprises [18F]DCFPyL.

10. The method of claim 7, wherein the agent comprises $^{99m}$Tc.

11. The method of claim 1, wherein the anatomical image comprises a CT image.

12. The method of claim 1, wherein the machine learning module implements a neural network.

13. The method of claim 12, wherein the machine learning module implements a fully convolutional CNN.

14. The method of claim 1, wherein step (c) comprises:
determining, by the processor, using a preliminary machine learning module, an initial VOI within the 3D anatomical image, the initial VOI corresponding to an anatomical region larger than and containing the target tissue region of interest;
using the initial VOI of the 3D anatomical image as the first input channel; and
using a sub-volume of the 3D functional image corresponding to the initial VOI as the second input channel.

15. The method of claim 1, wherein the machine learning module generates, as output, a likelihood map comprising a plurality of voxels, each corresponding to a voxel of the anatomical image and having a likelihood value representing a likelihood that the corresponding anatomical image voxel represents a physical volume within the target tissue region.

16. The method of claim 15, comprising generating the 3D segmentation mask based on the likelihood map.

17. The method of claim 1, comprising:
identifying, by the processor, using the 3D segmentation mask, a target VOI within the 3D functional image, the target VOI corresponding to the target tissue region; and
determining, by the processor, using intensities of voxels of the 3D functional image within the target VOI, one or more uptake metrics indicative of a quantity of an agent within the target tissue region.

18. The method of claim 17, comprising determining, by the processor, one or more risk index values using the one or more uptake metrics.

19. The method of claim 18, wherein at least one of the one or more risk index values is/are indicative of a risk of the subject having or developing a particular cancer.

20. The method of claim 18, wherein at least one of the one or more risk index values are indicative of a risk of the subject having or developing metastatic cancer.

21. The method of claim 18, wherein at least one of the one or more risk index values are indicative of a likelihood of the subject having a particular state of cancer.

22. A system for automatically processing 3D images to identify 3D volumes corresponding to a particular target tissue region within a subject, the system comprising:
a processor of a computing device; and
a memory having instructions stored thereon, wherein the instructions, when executed by the processor, cause the processor to:
(a) receive a 3D anatomical image of the subject obtained using an anatomical imaging modality, wherein the 3D anatomical image comprises a graphical representation of tissue within the subject;
(b) receive a 3D functional image of the subject obtained using a functional imaging modality;
(c) automatically generate using a machine learning module, a 3D segmentation mask that identifies, within the 3D anatomical image and/or the 3D functional image, a 3D volume of interest (VOI) corresponding to the target tissue region,
wherein the machine learning module: (i) receives at least two channels of input, said input channels comprising a first input channel corresponding to at least a portion of the 3D anatomical image and a second input channel corresponding to at least a portion of the 3D functional image and (ii) utilizes both the portion of the 3D anatomical image and the portion of the 3D functional image to perform image segmentation; and
(d) store and/or provide for display and/or further processing, the 3D segmentation mask.

* * * * *